US012154680B2

(12) United States Patent
Qiu et al.

(10) Patent No.: US 12,154,680 B2
(45) Date of Patent: Nov. 26, 2024

(54) ENDOSCOPIC IMAGE DISPLAY METHOD, APPARATUS, COMPUTER DEVICE, AND STORAGE MEDIUM

(71) Applicant: TENCENT TECHNOLOGY (SHENZHEN) COMPANY LIMITED, Shenzhen (CN)

(72) Inventors: Junwen Qiu, Shenzhen (CN); Zhongqian Sun, Shenzhen (CN); Xinghui Fu, Shenzhen (CN); Hong Shang, Shenzhen (CN); Han Zheng, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 428 days.

(21) Appl. No.: 17/674,126

(22) Filed: Feb. 17, 2022

(65) Prior Publication Data
US 2022/0172828 A1 Jun. 2, 2022

Related U.S. Application Data

(63) Continuation of application No. PCT/CN2020/124483, filed on Oct. 28, 2020.

(30) Foreign Application Priority Data

Jan. 20, 2020 (CN) .......................... 202010067143.X

(51) Int. Cl.
G16H 30/40 (2018.01)
G06T 7/00 (2017.01)
(Continued)

(52) U.S. Cl.
CPC ........... G16H 30/40 (2018.01); G06T 7/0014 (2013.01); G06T 7/11 (2017.01); G06V 10/454 (2022.01);
(Continued)

(58) Field of Classification Search
None
See application file for complete search history.

(56) References Cited

U.S. PATENT DOCUMENTS

2015/0065803 A1* 3/2015 Douglas ................. G06T 7/143
600/200
2016/0350912 A1* 12/2016 Koide ............... G02B 23/2484
(Continued)

FOREIGN PATENT DOCUMENTS

AU 2018101525 A4 * 11/2018
CN 103377376 A 10/2013
(Continued)

OTHER PUBLICATIONS

Y. Cai, Y. Li, C. Qiu, J. Ma and X. Gao, "Medical Image Retrieval Based on Convolutional Neural Network and Supervised Hashing," in IEEE Access, vol. 7, pp. 51877-51885, 2019, doi: 10.1109/ACCESS.2019.2911630 (Year: 2019).*
(Continued)

Primary Examiner — Vu Le
Assistant Examiner — Charles C L Penny
(74) Attorney, Agent, or Firm — Crowell & Moring LLP

(57) ABSTRACT

This application relates to an endoscopic image display method, apparatus, computer device, and storage medium, and relates to the field of machine learning technologies. The method acquiring an endoscopic image; locating a target region image in the endoscopic image, the target region image being a partial image comprising a target region; inputting the target region image into a coding network to obtain a semantic feature of the target region image, the coding network being a part of an image classification network, and the image classification network being a machine learning network obtained through training with first training images; matching the semantic feature of the target region image against semantic features of image (Continued)

samples to obtain a matching result, the matching result indicating a target image sample that matches the target region image; and displaying the endoscopic image and the matching result in an endoscopic image display interface.

17 Claims, 12 Drawing Sheets

(51) Int. Cl.
   *G06T 7/11* (2017.01)
   *G06V 10/44* (2022.01)

(52) U.S. Cl.
   CPC ............... *G06T 2207/10068* (2013.01); *G06T 2207/20081* (2013.01); *G06T 2207/20084* (2013.01)

(56) References Cited

U.S. PATENT DOCUMENTS

| | | | |
|---|---|---|---|
| 2020/0005072 | A1 | 1/2020 | Tan et al. |
| 2021/0090247 | A1* | 3/2021 | Jeon ........................ G06N 3/047 |

FOREIGN PATENT DOCUMENTS

| | | | |
|---|---|---|---|
| CN | 106934799 | A | 7/2017 |
| CN | 107679250 | A | 2/2018 |
| CN | 107832335 | A | 3/2018 |
| CN | 108596884 | A | 9/2018 |
| CN | 108852268 | A | 11/2018 |
| CN | 109410185 | A | 3/2019 |
| CN | 109903314 | A | 6/2019 |
| CN | 109948733 | A | 6/2019 |
| CN | 109978002 | A | 7/2019 |
| CN | 110136199 | A | 8/2019 |
| CN | 110414607 | A | 11/2019 |
| CN | 110475503 | A | 11/2019 |
| CN | 110689025 | A | 1/2020 |
| CN | 111275041 | A | 6/2020 |

OTHER PUBLICATIONS

Y. Zheng et al., "Localisation of colorectal polyps by convolutional neural network features learnt from White Light and narrow band endoscopic images of multiple databases," 2018 40th Annual International Conference of the IEEE Engineering in Medicine and Biology Society (EMBC), Jul. 2018. (Year: 2018).*

K. L. Wiggers, A. S. Britto, L. Heutte, A. L. Koerich and L. S. Oliveira, "Image Retrieval and Pattern Spotting using Siamese Neural Network," 2019 International Joint Conference on Neural Networks (IJCNN), Budapest, Hungary, 2019, pp. 1-8, doi: 10.1109/IJCNN.2019.8852197. (Year: 2019).*

X. He, Y. Tang, L. Wang and P. Chen, "End-to-End Feature Learning for Multi-label Image Retrieval," 2019 International Conference on Intelligent Computing, Automation and Systems (ICICAS), Chongqing, China, 2019, pp. 293-297, doi: 10.1109/ICICAS48597.2019.00070 (Year: 2019).*

A. Qayyum, S. M. Anwar, M. Awais, and M. Majid, "Medical image retrieval using deep convolutional neural network," Neurocomputing, vol. 266, pp. 8-20, Nov. 2017. doi:10.1016/j.neucom.2017.05.025 (Year: 2017).*

Y. Zheng et al., "Localisation of colorectal polyps by convolutional neural network features learnt from White Light and narrow band endoscopic images of multiple databases," 2018 40th Annual Int. Conf. of the IEEE Engr. in Medicine and Biology Society (EMBC), Jul. 2018. doi:10.1109/embc.2018.8513337 (Year: 2018).*

First Chinese Office Action with English concise explanation of relevance regarding 202010067143.X dated May 23, 2022.

Second Chinese Office Action with English concise explanation of relevance regarding 202010067143.X dated Sep. 5, 2022.

International Search Report with English translation and Written Opinion regarding PCT/CN2020/124483 dated Feb. 10, 2021, 9 pages.

* cited by examiner

ENDOSCOPIC IMAGE DISPLAY METHOD, APPARATUS, COMPUTER DEVICE, AND STORAGE MEDIUM

RELATED APPLICATION

This application is a continuation application of PCT Patent Application No. PCT/CN2020/124483, filed on Oct. 28, 2020, which claims priority to Chinese Patent Application No. 202010067143.X, filed on Jan. 20, 2020, both of which are incorporated herein by reference in their entireties.

FIELD OF THE TECHNOLOGY

The embodiments of this application relate to the field of machine learning technology, and in particular, to an endoscopic image display method, device, computer device, and storage medium.

BACKGROUND OF THE DISCLOSURE

With the continuous development of medical technology, endoscopes (such as gastroscopes or colonoscopes, etc.) have gradually become an important means to assist doctors in diagnosing gastrointestinal diseases.

In related technologies, the operator of the endoscope equipment (such as a doctor or nurse) operates the lens of the endoscope to penetrate into the patient's digestive tract, and the lens of the endoscope captures real-time images of the digestive tract in the patient's body, and the images of the digestive tract are displayed on the display interface of an external display, for the doctor to make a preliminary diagnosis of the health condition of the patient's digestive tract based on the images of the digestive tract.

However, endoscopy-assisted diagnosis requires experienced doctors. At present, many doctors lack the ability to accurately diagnose gastrointestinal diseases with the assistance of endoscopes, resulting in low accuracy of endoscopy-assisted diagnosis.

SUMMARY

Embodiments of this application provide an endoscopic image display method, apparatus, computer device, and storage medium, which can improve the accuracy of endoscopy-assisted diagnosis.

The present disclosure describes a method for displaying an endoscopic image. The method includes acquiring, by a device, an endoscopic image captured by an endoscope. The device includes a memory storing instructions and a processor in communication with the memory. The method also includes locating, by the device, a target region image in the endoscopic image, the target region image being a partial image comprising a target region in the endoscopic image; inputting, by the device, the target region image into a coding network to obtain a semantic feature of the target region image, the coding network being a part of an image classification network, the coding network configured to extract image features, and the image classification network being a machine learning network obtained through training with first training images; matching, by the device, the semantic feature of the target region image against semantic features of image samples to obtain a matching result, the matching result indicating a target image sample that matches the target region image among the image samples; and displaying, by the device, the endoscopic image and the matching result in an endoscopic image display interface.

The present disclosure describes an apparatus for displaying an endoscopic image. The apparatus includes a memory storing instructions; and a processor in communication with the memory. When the processor executes the instructions, the processor is configured to cause the apparatus to perform: acquiring an endoscopic image captured by an endoscope; locating a target region image in the endoscopic image, the target region image being a partial image comprising a target region in the endoscopic image; inputting the target region image into a coding network to obtain a semantic feature of the target region image, the coding network being a part of an image classification network, the coding network configured to extract image features, and the image classification network being a machine learning network obtained through training with first training images; matching the semantic feature of the target region image against semantic features of image samples to obtain a matching result, the matching result indicating a target image sample that matches the target region image among the image samples; and displaying the endoscopic image and the matching result in an endoscopic image display interface.

The present disclosure describes a non-transitory computer-readable storage medium, storing computer-readable instructions. The computer-readable instructions, when executed by a processor, are configured to cause the processor to perform: acquiring an endoscopic image captured by an endoscope; locating a target region image in the endoscopic image, the target region image being a partial image comprising a target region in the endoscopic image; inputting the target region image into a coding network to obtain a semantic feature of the target region image, the coding network being a part of an image classification network, the coding network configured to extract image features, and the image classification network being a machine learning network obtained through training with first training images; matching the semantic feature of the target region image against semantic features of image samples to obtain a matching result, the matching result indicating a target image sample that matches the target region image among the image samples; and displaying the endoscopic image and the matching result in an endoscopic image display interface.

According to one aspect, an endoscopic image display method is provided. The method is executed by a computer device. The method includes:

acquiring an endoscopic image captured by an endoscope;

locating a target region image in the endoscopic image, the target region image being a partial image including a target region in the endoscopic image;

inputting the target region image into a coding network to obtain a semantic feature of the target region image outputted by the coding network, the coding network being a network part configured to extract image features in an image classification network, and the image classification network being a machine learning network obtained through training with first training images and image categories of the first training images;

matching the semantic feature of the target region image against semantic features of image samples to obtain a matching result, the matching result being used for indicating a target image sample that matches the target region image among the image samples; and displaying the endoscopic image and the matching result in an endoscopic image display interface.

According to another aspect, an endoscopic image display method is provided. The method is executed by a computer device. The method includes:
- displaying a first endoscopic image in an endoscopic image display interface, the first endoscopic image being an image captured by an endoscope in a white light mode;
- in response to switching of a shooting mode of the endoscope to a narrow band imaging (NBI) mode, displaying a second endoscopic image in the endoscopic image display interface, the second endoscopic image being an image captured by the endoscope in the NBI mode; and
- displaying a matching result corresponding to the second endoscopic image in the endoscopic image display interface, the matching result being used for indicating a target image sample that matches a target region image in the second endoscopic image.

According to another aspect, an endoscopic image display apparatus is provided. The apparatus is applicable to a computer device. The apparatus includes:
- an endoscopic image acquisition module, configured to acquire an endoscopic image captured by an endoscope;
- a region image localizing module, configured to locate a target region image in the endoscopic image, the target region image being a partial image including a target region in the endoscopic image;
- a semantic feature extraction module, configured to input the target region image into a coding network to obtain a semantic feature of the target region image outputted by the coding network, the coding network being a network part configured to extract image features in an image classification network, and the image classification network being a machine learning network obtained through training with first training images and image categories of the first training images;
- a matching module, configured to match the semantic feature of the target region image against semantic features of image samples to obtain a matching result, the matching result being used for indicating a target image sample that matches the target region image among the image samples; and
- a display module, configured to display the endoscopic image and the matching result in an endoscopic image display interface.

Optionally, the matching module includes:
- a matching score acquisition sub-module, configured to input the semantic feature of the target region image and the semantic features of the image samples into a matching network, and obtain matching scores between the target region image and the image samples outputted by the matching network, the matching network being obtained by training with semantic feature pairs each marked with a matching tag, each of the semantic feature pairs including semantic features of two images, and the matching tag being used for indicating whether the corresponding semantic feature pairs match;
- an image sample determination sub-module, configured to determine the target image sample based on the matching scores between the target region image and the image samples; and
- a matching result acquisition sub-module, configured to acquire the matching result based on the target image sample. In some implementations, the matching tag may indicate a matching score or matching degree, indicating how close the matching is.

Optionally, the image sample determination sub-module is configured to:
- sort the image samples in descending order of the corresponding matching scores, and use top n image samples as the target image samples, wherein n≥1, and n is an integer; or
- use the image sample with the corresponding matching score higher than a matching score threshold among the image samples as the target image sample; or
- sort the image samples in descending order of the corresponding matching scores, and use the image sample with the corresponding matching score higher than a matching score threshold among top n image samples as the target image sample.

Optionally, the matching result includes at least one of the following:
- the target image sample;
- the image category corresponding to the target image sample; and
- a matching degree between the target image sample and the target region image.

Optionally, the apparatus further includes:
- a second display module, configured to display a region mark corresponding to the endoscopic image in the endoscopic image display interface, the region mark being used for indicating the target region in the endoscopic image.

Optionally, the region image localizing module includes:
- a region coordinate acquisition sub-module, configured to input the endoscopic image into a target region locating network to obtain region coordinates outputted by the target region locating network, the target region locating network being a machine learning network obtained through training with second training images, and the second training images being each marked with a target region; and
- a first region image acquisition sub-module, configured to acquire an image corresponding to the region coordinates in the endoscopic image as the target region image.

Optionally, the region image localizing module includes:
- a user operation receiving sub-module, configured to receive a framing operation performed by a user in the endoscopic image; and
- a second region image acquisition sub-module, configured to acquire an image of a region corresponding to the framing operation in the endoscopic image as the target region image.

Optionally, the region image localizing module is configured to perform the operation of locating a target region image in the endoscopic image, in response to an image mode of the endoscopic image being a narrow band imaging (NBI) mode.

Optionally, the apparatus further includes:
- an image mode information acquisition module, configured to input the endoscopic image into an image mode classification network, and obtaining image mode information outputted by the image mode classification network, the image mode classification network being a machine learning network obtained through training with third training images, each of the third training images being marked with an image mode, and the image mode information being used for indicating whether the image mode of the endoscopic image is the NBI mode.

Optionally, the apparatus further includes:

an operation status acquisition module, configured to acquire an operation status of the endoscope during the capturing of the endoscopic image; and determine that the image mode of the endoscopic image is the NBI mode, in response to the operation status being the NBI state.

Optionally, the apparatus further includes:

an image quality information acquisition module, configured to acquire image quality information of the endoscopic image, the image quality information including at least one of degree of blurring, exposure and hue abnormality, or effective resolution; and a regional image positioning module, configured to perform the operation of locating a target region image in the endoscopic image, in response to the image quality information satisfying an image quality threshold.

According to a fourth aspect, an endoscopic image display apparatus is provided. The apparatus is applicable to a computer device. The apparatus includes:

a first display module, configured to display a first endoscopic image in an endoscopic image display interface, the first endoscopic image being an image captured by an endoscope in a white light mode;

a second display module, configured to, in response to switching of a shooting mode of the endoscope to a narrow band imaging (NBI) mode, display a second endoscopic image in the endoscopic image display interface, the second endoscopic image being an image captured by the endoscope in the NBI mode; and a third display module, configured to display a matching result corresponding to the second endoscopic image in the endoscopic image display interface, the matching result being used for indicating a target image sample that matches a target region image in the second endoscopic image.

According to a fifth aspect, a computer device is provided. The computer device includes a processor and a memory, the memory storing at least one instruction, at least one program, a code set, or an instruction set, the at least one instruction, the at least one program, the code set, or the instruction set being loaded and executed by the processor to implement the endoscopic image display method described above.

According to a sixth aspect, a computer-readable storage medium is provided. The storage medium stores at least one instruction, at least one program, a code set, or an instruction set, the at least one instruction, the at least one program, the code set, or the instruction set being loaded and executed by a processor to implement the endoscopic image display method described above.

The technical solutions provided in this application may include the following beneficial effects:

By acquiring an endoscopic image captured by an endoscope, locating a target region image in the endoscopic image, inputting the target region image into a coding network to obtain a semantic feature of the target region image outputted by the coding network, matching the semantic feature of the target region image against semantic features of image samples to obtain a matching result, and displaying the endoscopic image and the matching result in an endoscopic image display interface, the accuracy of diagnosis with the assistance of the endoscope is improved by localizing and matching the image of the lesion in the endoscopic image during the use of the endoscope.

It is to be understood that the foregoing general descriptions and the following detailed descriptions are merely exemplary and explanatory, and are not intended to limit this application.

BRIEF DESCRIPTION OF THE DRAWINGS

Accompanying drawings herein are incorporated into this specification and constitute a part of this specification, show embodiments that conform to this application, and are used for describing a principle of this application together with this specification.

DESCRIPTION OF EMBODIMENTS

Figure 1:
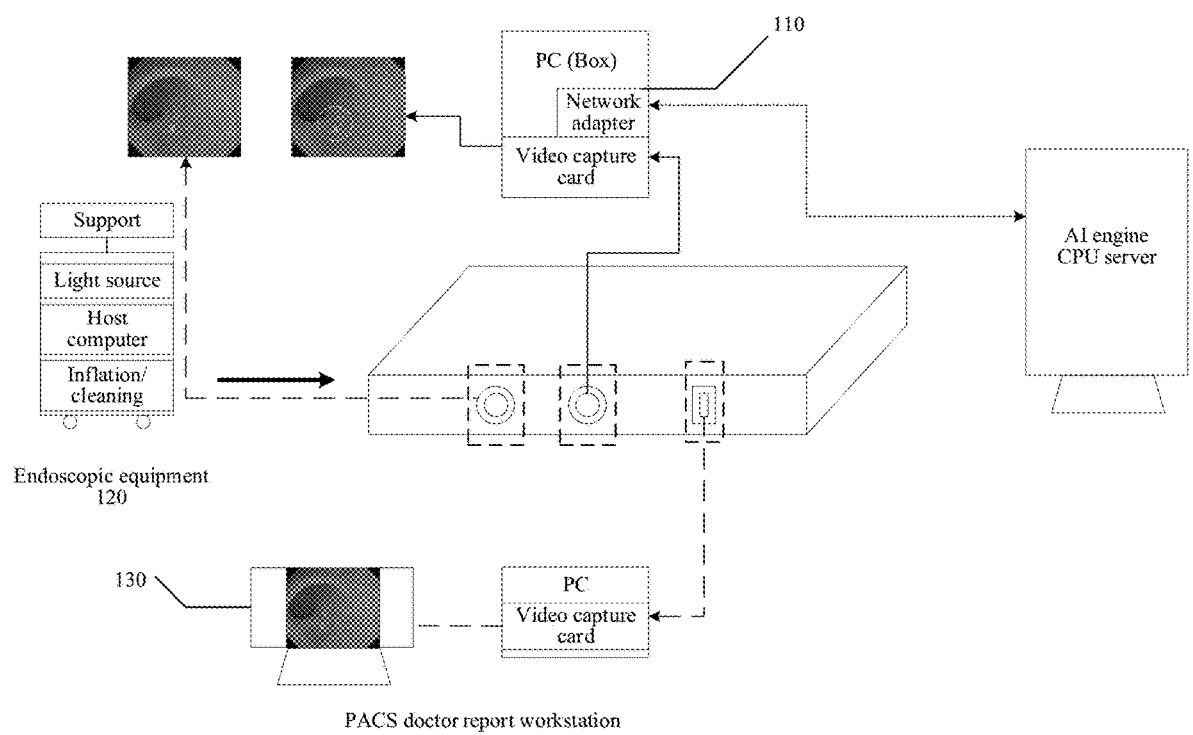
FIG. 1 is an architectural diagram showing image recognition and image display according to an exemplary embodiment.

Exemplary embodiments are described in detail herein, and examples of the exemplary embodiments are shown in the accompanying drawings. When the following descriptions relate to the accompanying drawings, unless otherwise indicated, same numbers in different accompanying drawings represent same or similar elements. The implementations described in the following exemplary embodiments do not represent all implementations that are consistent with this application. On the contrary, the implementations are merely examples of apparatuses and methods that are described in detail in the appended claims and that are consistent with some aspects of this application.

The embodiments of the application propose an efficient and high-accuracy endoscopy-assisted diagnosis solution, which can help users and their doctors quickly identify possible digestive tract diseases (such as early gastric cancer) by positioning the image of the lesion region in the endoscopic image and matching the image of the lesion region with known image samples. For convenience of understanding, terms in the embodiments of this application are described.

1) Endoscope

In this application, an endoscope refers to a commonly used medical instrument composed of a bendable part, a light source, and a lens. The endoscope can enter the human body through the natural orifice of the human body or through a small incision made by surgery. When in use, the endoscope can be introduced into the organ to be examined for the user to directly observe the changes in the relevant part.

Commonly used endoscopes include gastroscopes, colonoscopes and so on.

A gastroscope is an endoscope that uses a slender, soft tube to extend from the pharynx into the stomach, so that the lens on the head of the tube can capture images of the digestive tract in the patient's body in real time. With the assistance of a gastroscope, the doctor can directly observe the lesions of the esophagus, stomach and duodenum through the screen of an external display. Gastroscopy allows the doctor to directly observe the true condition of the examined part, and can further confirm the diagnosis by biopsy and cytology of suspicious lesions, and is the first choice for examining upper gastrointestinal lesions.

2) Lesion Region

It usually refers to the part of the body where a disease occurs, and the lesion region of the digestive tract disease is the region where the disease occurs in the digestive tract organs. For example, if protruding tissue grows on the surface of the gastric mucosa, the gastric mucosal region corresponding to the protruding tissue is the lesion region of gastric polyposis; For another example, if the duodenum of the stomach digests its own mucosa under the invasion of high gastric acid and pepsin to form local inflammatory defects, the region corresponding to the digested duodenal mucosal epithelium is the lesion region of the duodenal ulcer.

3) Narrow Band Imaging (NBI)

NBI, also known as narrow-band imaging endoscopy, is an emerging endoscopic technology that uses a filter to filter out the broadband spectrum in red, blue, and green light waves emitted by the endoscope light source, and keeping only the narrow-band spectrum for diagnosis of various digestive tract diseases. Image obtained after the NBI mode is enabled can not only accurately display the morphology of the mucosal epithelium of the digestive tract, such as the structure of the epithelial fossa, but also the morphology of the epithelial vascular network. This new technology can better help endoscopists distinguish gastrointestinal epithelium, changes in vascular morphology in gastrointestinal inflammation, and irregular changes in early gastrointestinal tumors, thereby improving the accuracy of endoscopic diagnosis.

4) Loss Function

The loss function or cost function is a function that maps the value of a random event or its related random variable to a non-negative real number to represent the "risk" or "loss" of the random event. In applications, the loss function is usually associated with optimization problems as a learning criterion, that is, the model is solved and evaluated by minimizing the loss function.

5) Artificial Intelligence (AI)

AI is a theory, method, technology, and application system that uses a digital computer or a machine controlled by the digital computer to simulate, extend, and expand human intelligence, perceive an environment, acquire knowledge, and use knowledge to obtain an optimal result. In other words, AI is a comprehensive technology in computer science and attempts to understand the essence of intelligence and produce a new intelligent machine that can react in a manner similar to human intelligence. AI is to study the design principles and implementation methods of various intelligent machines, to enable the machines to have the functions of perception, reasoning, and decision-making.

AI technology is a comprehensive discipline, covering a wide range of fields including both a hardware-level technology and a software-level technology. Basic AI technologies generally include technologies such as sensors, dedicated AI chips, cloud computing, distributed storage, big data processing technologies, operating/interaction systems, and mechatronics. AI software technologies mainly include a computer vision technology, a speech processing technology, a natural language processing (NLP) technology, machine learning/deep learning, and the like. The solutions provided in the embodiments of this application mainly involve technologies such as machine learning/deep learning of AI.

6) Machine Learning (ML)

ML is a multi-field interdisciplinary subject involving the probability theory, statistics, the approximation theory, convex analysis, the algorithm complexity theory, and the like. The ML specializes in studying how a computer simulates or implements a human learning behavior to obtain new knowledge or skills, and reorganize an existing knowledge structure, so as to keep improving its performance. ML is the core of AI, is a basic way to make the computer intelligent, and is applied to various fields of AI. The machine learning and deep learning generally include technologies such as an artificial neural network, a belief network, reinforcement learning, transfer learning, inductive learning, and learning from demonstrations.

7) AI Box

The AI box is a set of hardware equipment and services deployed in a hospital. An AI engine service and a video capture card are integrated in the AI box. The AI box can acquire a real-time video stream of an endoscope, and input the video stream to the AI engine service, to localize in real time a lesion in an endoscopic image and immediately analyze a probability of occurrence of an early cancer by AI.

The solution of the embodiments of this application includes an identification stage and a display stage. FIG. 1 is an architectural diagram showing image recognition and image display according to an exemplary embodiment. As shown in FIG. 1, in the image recognition stage, an image recognition device 110 performs real-time lesion recognition based on an endoscopic image inputted by an endoscopic device 120. The image recognition device 110 may be an AI box. The image recognition device may include a video capture module, an image recognition module, and an image output module. The video capture module is configured to acquire in real time an image captured by an endoscope and input the image into the image recognition module. The video capture module may be implemented as a video capture card shown in FIG. 1. The image recognition module is configured to perform recognition processing on the image inputted to the image recognition device to obtain a recognition result. The image recognition module can be implemented as an AI engine and a CPU server shown in FIG. 1. In a possible situation, the AI engine and the CPU server may be integrated in the AI box, or the AI engine and the CPU server may exchange information with the AI box in a wired or wireless manner. The image output module is configured to output the recognition result obtained by the image recognition module to the image display apparatus 130 for displaying. The image display apparatus 130 may be a built-in display module of the image recognition device 110 or an external image display apparatus 120 connected to the image recognition device 110. In the image display stage, the image display apparatus 130 displays the endoscopic image and the recognition result of the image recognition device 110 in an image display interface.

The image recognition device 110 may be a computer device with machine learning capabilities. The computer device may be a stationary computer device such as a personal computer, a server, or a stationary medical device (such as the aforementioned AI box), or the computer device may also be a mobile computer device such as a tablet computer, an e-book reader, or a portable medical device.

Optionally, the image recognition device 110 and the image display apparatus 130 may be the same device, or the image recognition device 110 and the image display apparatus 130 may be different devices. Moreover, when the image recognition device 110 and the image display apparatus 130 are different devices, the image recognition device 110 and the image display apparatus 130 may be devices of the same type. For example, the image recognition device 110 and the image display apparatus 130 may both be personal computers. Alternatively, the image recognition device 110 and the image display apparatus 130 may also be devices of different types. For example, the image recognition device 110 may be an AI box, and the image display apparatus 120 may be a stationary medical device or a portable medical device. For example, the image display apparatus may be a Picture Archiving & Communication System (PACS) doctor report workstation shown in FIG. 1. The specific types of the image recognition device 110 and the image display apparatus 130 are not limited in the embodiments of this application.

In the embodiments of this application, this application is described using an example where the image display apparatus is an external device connected to the image recognition device (for example, an AI box).

Figure 2:
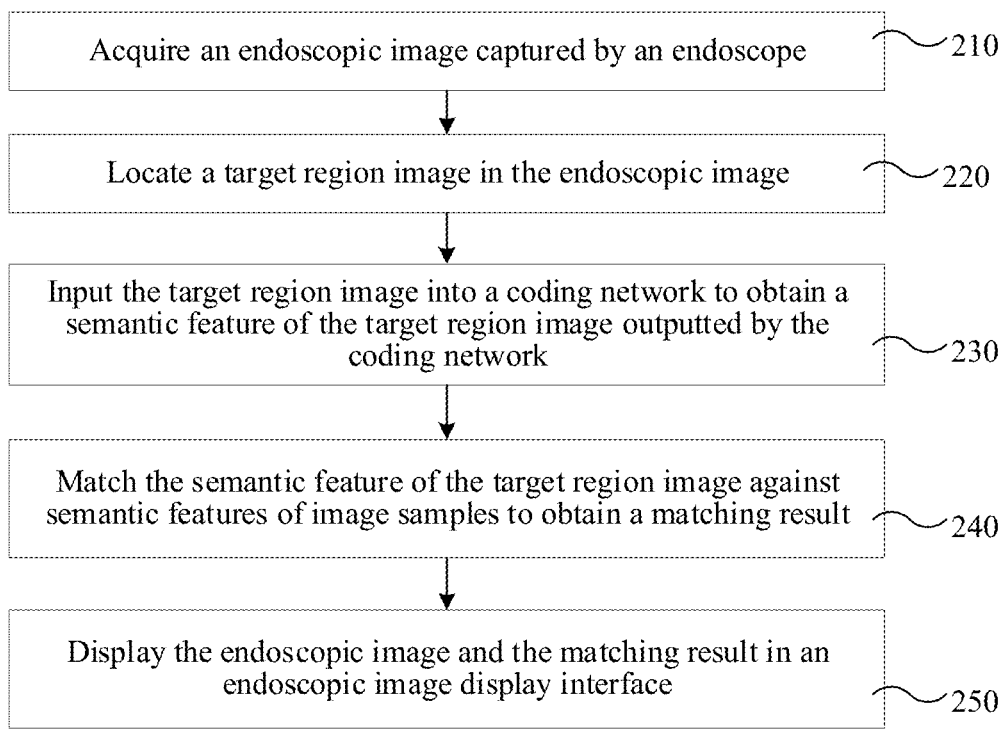
FIG. 2 is a flowchart of an endoscopic image display method according to an exemplary embodiment of this application.

FIG. 2 is a flowchart of an endoscopic image display method according to an exemplary embodiment of this application. The endoscopic image display method may be applied in a computer device. For example, the computer device may be the image recognition device shown in FIG. 1. As shown in FIG. 2, the endoscopic image display method may include the following steps:

Step 210: Acquire an endoscopic image captured by an endoscope.

The endoscopic image captured by the endoscope may be a white light image or an NBI image. The NBI image refers to an image captured after the broadband spectrum in the red, blue, and green light waves emitted by an endoscope light source is filtered out using a filter during the endoscopic image capturing process. Whether the endoscopic image captured by the endoscope is a white light image or an NBI image may be adjusted by a medical worker by changing the working mode of the endoscope. When the working mode of the endoscope is a white light mode, the image captured by the endoscope is a white light image. When the working mode of the endoscope is an NBI mode, the image captured by the endoscope is an NBI image.

Step 220: Locate a target region image in the endoscopic image, the target region image being a partial image including a target region in the endoscopic image.

When the endoscopic image shows that there may be a suspicious lesion region, the computer device may use an image of a region where the suspicious lesion region is located in the endoscopic image as the target region image, and locate the position of the target region image in the endoscopic image.

Step 230: Input the target region image into a coding network to obtain a semantic feature of the target region image outputted by the coding network. The coding network may be a portion of an image classification network; and the coding network is configured to extract image features. The image classification network may be a machine learning network obtained through training with first training images and image categories of the first training images.

In some other implementations, the coding network is a part of an image classification network, the coding network is configured to extract image features, and the image classification network is a machine learning network obtained through training with first training images.

The coding network may be a convolutional network (such as a fully convolutional network), and the coding network is configured to extract an image feature, so as to obtain the semantic feature of the target region image inputted to the coding network.

In the embodiments of this application, the coding network may be a part of the image classification network, and the image classification network may be composed of the coding network and a classification network. In the training process of the image classification network, a first training image and an image category of the first training image may be inputted to a model training device to train the image classification network. For example, a loss function may be calculated based on an output result of the image classification network and the image category of the first training image, and parameters in the image classification network may be adjusted according to the loss function, so that the output result of the image classification network obtained by training is as close to the image category of the first training image as possible. The loss function is used for normalizing a relationship between the output result of the image classification network and the image category of the first training image.

In the embodiments of this application, the first training image may be a region image marked in the endoscopic image, and the image category of the first training image may be an image type corresponding to the region image, where the image type indicates whether the region image is an image of a target region, for example, a lesion region.

Step 240: Match the semantic feature of the target region image against semantic features of image samples to obtain a matching result, the matching result being used for indicating a target image sample that matches the target region image among the image samples.

The semantic features of the image samples refer to semantic features corresponding to the image samples that are obtained in advance by inputting the image samples into the same coding model as the target region image.

Optionally, each image sample has a corresponding lesion attribute, and the matching result of the semantic feature of the target region image and the semantic features of the image samples may indicate the lesion attribute that the target region image may correspond to.

Step 250: Display the endoscopic image and the matching result in an endoscopic image display interface.

The endoscopic image display interface may be a display screen of an external image display apparatus connected to the computer device. The endoscopic image display interface may display in real time an image captured by the endoscope, or an image obtained by the computer device after processing the image captured by the endoscope, for example, an image marked with the position of the target region image. In the embodiments of this application, the matching result may also be displayed in the endoscopic image display interface.

Optionally, the matching result may include a lesion attribute that the target region image may correspond to and that is obtained by a matching network, and/or an image of an image sample corresponding to the matching result.

Based on the above, with the endoscopic image display method provided by this application, by acquiring an endoscopic image captured by an endoscope, locating a target region image in the endoscopic image, inputting the target region image into a coding network to obtain a semantic feature of the target region image outputted by the coding network, matching the semantic feature of the target region image against semantic features of image samples to obtain a matching result, displaying the endoscopic image and the matching result in an endoscopic image display interface, the accuracy of diagnosis with the assistance of the endoscope is improved by localizing and matching the image of the lesion in the endoscopic image during the use of the endoscope.

Figure 3:
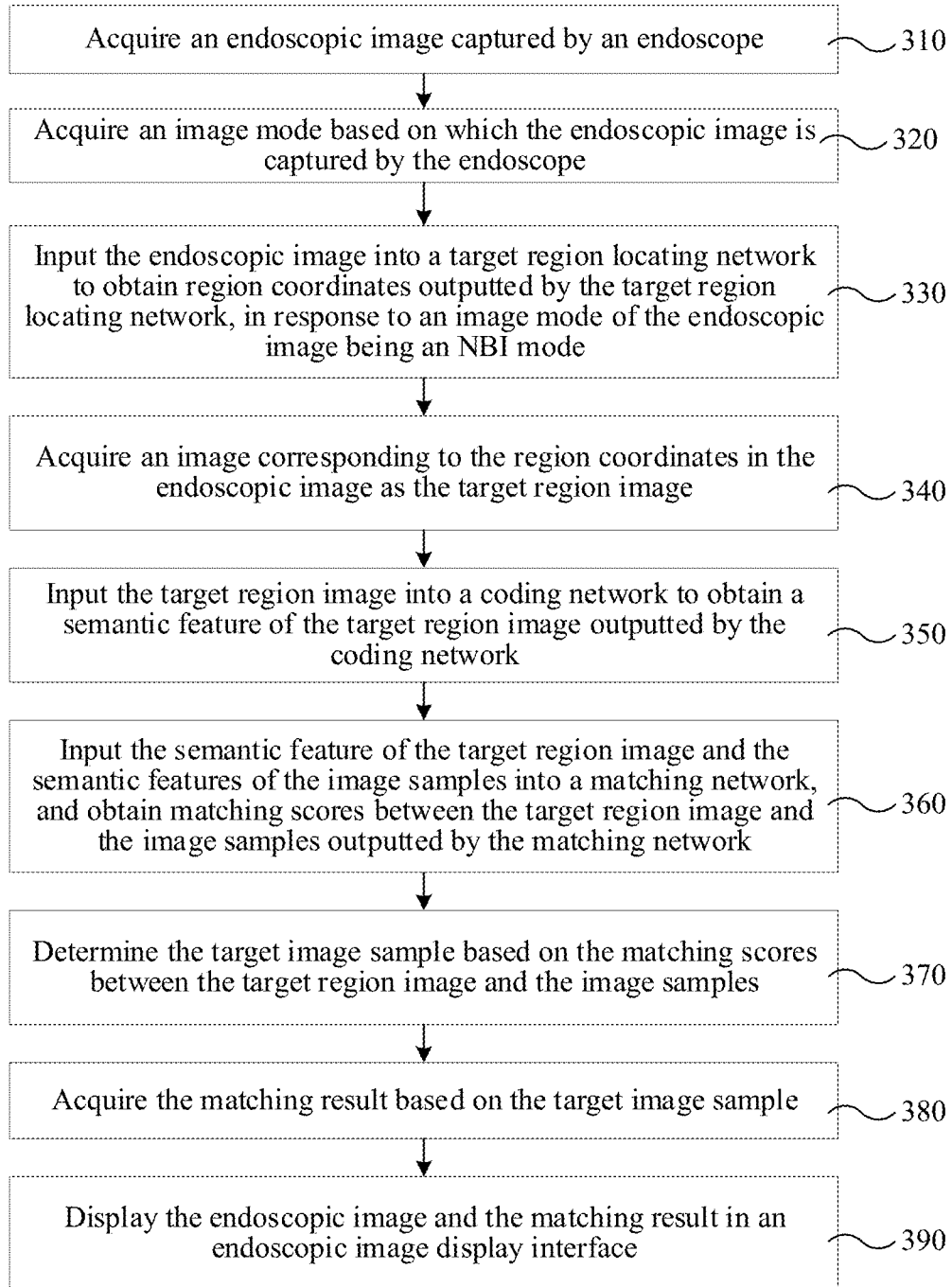
FIG. 3 is a flowchart of an endoscopic image display method according to an exemplary embodiment of this application.

Based on the endoscopic image display method shown in FIG. 2, when the step of locating a target region image in the endoscopic image is executed by the computer device, FIG. 3 is a flowchart of an endoscopic image display method according to an exemplary embodiment of this application. The endoscopic image display method may be applied in a computer device, for example, the image recognition device shown in FIG. 1. As shown in FIG. 3, the endoscopic image display method may include the following steps:

Step 310: Acquire an endoscopic image captured by an endoscope.

For example, taking a computer device including an AI box and an AI engine as an example, when a video capture card in the AI box captures a video, the video capturing process may be expressed as: the AI box acquires a real-time video stream of the endoscope and inputs the real-time video stream of the endoscope into the AI engine server which is connected to or integrated in the AI box, and correspondingly the AI engine server acquires the endoscopic image captured by the endoscope.

Step 320: Acquire an image mode based on which the endoscopic image is captured by the endoscope.

The image mode of the endoscopic image may be switched by the medical staff through manual adjustment. For example, when the medical staff finds a suspicious lesion by observing an endoscopic image in a white light mode, the medical staff can switch the white light mode to an NBI mode, where compared with an image captured in the white light mode, an image captured in the NBI mode can more clearly show information such as the distribution of blood vessels and glandular orifices; and in the NBI mode, further observes more details of the suspicious lesion in the endoscopic image, so as to better diagnose the suspicious lesion.

Therefore, optionally, the process of acquiring an image mode based on which the endoscopic image is captured by the endoscope may be implemented as:

acquiring an operation status of the endoscope during the capturing of the endoscopic image; and determining that the image mode of the endoscopic image is the NBI mode, in response to the operation status being the NBI state.

In some other implementations, the process of acquiring an image mode based on which the endoscopic image is captured by the endoscope may include a portion or all of the following: acquiring an operation status of the endoscope during the capturing of the endoscopic image; determining whether the operation status is an NBI state; in response to determining that the operation status is the NBI state, determining that the image mode of the endoscopic image is an NBI mode.

For example, the computer device may acquire the operation status of the endoscope when capturing the endoscopic image based on a user operation of mode selection performed by the medical staff. When the user operation indicates that the endoscope is in the white light mode, the image mode of the endoscopic image captured by the endoscope in this mode is the white light mode. When the user operation indicates that the endoscope is in the NBI mode, the image mode of the endoscopic image captured by the endoscope in this mode is the NBI mode.

Alternatively, optionally, the computer device may input the endoscopic image into an image mode classification network, and obtain image mode information outputted by the image mode classification network, the image mode classification network being a machine learning network obtained through training with third training images, the image mode information being used for indicating whether the image mode of the endoscopic image is the NBI mode, and each of the third training images being marked with an image mode.

Optionally, the image mode classification network may be a dense convolutional network (DenseNet), which is configured to classify and recognize endoscopic images, and the image mode classification network may be obtained in advance by training with a machine learning model.

For example, in the training process, an endoscopic image sample and a corresponding image mode may be inputted into the model training device to construct an image mode classification network, a loss function may be calculated based on an output result of the image mode classification network and the corresponding image mode, and parameters in the image mode classification network may be adjusted according to the loss function, so that the output result of the image mode classification network obtained by training is as close to the image mode of the endoscopic image sample as possible.

During the use of the image mode classification network, the computer device may input an endoscopic image into the image mode classification network, and accordingly the image mode classification network may output an image mode corresponding to the endoscopic image.

Optionally, the image mode classification network may scale the input endoscopic image so that the size of the scaled endoscopic image meets the requirements of the image mode classification network. For example, if the size of the endoscopic image required by the image mode classification network is 224*224, the size of the input endoscopic image is scaled to 224*224 before the image mode is determined.

In various embodiments, an image mode classification network may include a neural network architecture/structure showing in Table 1.

TABLE 1

| Number of layers | Output size | Dense convolutional network-40 |
|---|---|---|
| Convolution Pooling layer | 112 × 112<br>56 × 56 | 7 × 7 transformation with a stride of 2<br>3 × 3 maximum pooling, with a stride of 2 |
| Dense block (1) | 56 × 56 | $\begin{bmatrix} 1 \times 1 conv \\ 3 \times 3 conv \end{bmatrix} \times 6$ |
| Transition layer (1) | 56 × 56<br>28 × 28 | 1 × 1 conv<br>2 × 2 average pooling, with a stride of 2 |
| Dense block (2) | 28 × 28 | $\begin{bmatrix} 1 \times 1 conv \\ 3 \times 3 conv \end{bmatrix} \times 6$ |
| Transition layer (2) | 28 × 28<br>14 × 14 | 1 × conv<br>2 × 2 average pooling, with a stride of 2 |
| Dense block (3) | 14 × 14 | $\begin{bmatrix} 1 \times 1 conv \\ 3 \times 3 conv \end{bmatrix} \times 6$ |
| Classification layer | 1 × 1 | 7 × 7 global average pooling<br>2D fully connected, normalized exponential function |

Note:
The transformation layer is a BN-ReLU-Conv sequence

In various embodiments in the present disclosure, the image mode classification network may include lower-level feature combinations, such as blood vessel color, etc., and thus, when setting the combination of depth and width of the dense convolutional network structure, a wider and shallower mode may be used, and finally the network structure used may be the above-mentioned DenseNet-40 (dense convolutional network structure-40). Then the network parameters are tuned, for example, the growth-rate is set to 48, and the compression ratio of a feature after passing through the transformation layer is 0.5.

Optionally, before the computer device locates the target region image in the endoscopic image, the method further includes:

acquiring image quality information of the endoscopic image, the image quality information including at least one of degree of blurring, exposure and hue abnormality, or effective resolution; and performing the operation of locating a target region image in the endoscopic image, in response to the image quality information satisfying an image quality threshold.

During the image capturing process of the endoscope, the acquired endoscopic image may contain blurred images caused by blurred shooting or undigested food residues in the digestive tract. Because the existence of these blurred images will cause serious errors in subsequent analysis, it is necessary to filter out low-quality images from the images acquired by the endoscope. The low-quality images may include but are not limited to the following three situations: blurred images, images with abnormal hues and/or overexposure/underexposure, and low-resolution images.

Figure 4:
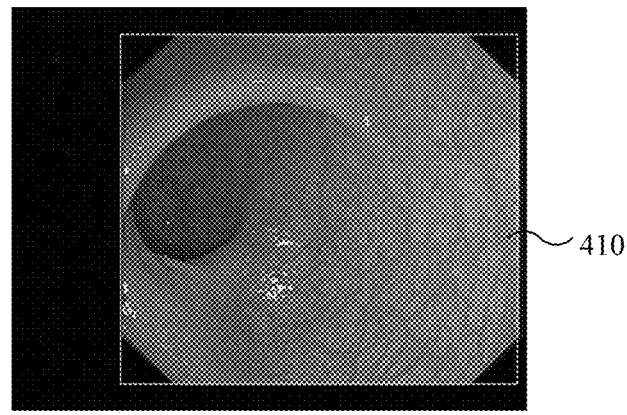
FIG. 4 is a schematic diagram of an effective pixel area according to an exemplary embodiment of this application.

The computer device may identify the low-resolution images by calculating an effective pixel area in the image, where the effective pixel area refers to the area of the image after the upper, lower, left, and right black borders of the image are cut off. FIG. 4 is a schematic diagram of an effective pixel area according to an exemplary embodiment of this application. As shown in FIG. 4, a region 410 in the interface of FIG. 4 is the effective pixel area. In some implementations, the effective pixel area may not include upper, lower, left, and right black borders, which are outside the region 410 in FIG. 4. In some other implementations, the effective pixel area may include the region 410 within and surrounded by upper, lower, left, and right white lines in FIG. 4.

The process of cutting the black borders (e.g., in FIG. 4) may be implemented by the computer device by analyzing the gray value distribution of each row or column of pixel values in the image. When a proportion of gray values lower than a preset threshold in the gray value distribution of a certain row or column of pixel values in the image reaches a certain threshold, it is determined that the row or column needs to be cut off. For example, when the proportion of gray values lower than a preset threshold in the gray value distribution of a certain row or column of pixel values in the image reaches 50%, it is determined that the row or column needs to be cut off. The computer device determines whether the effective pixel area obtained after the black borders are cut off, and if the effective pixel area is less than a certain threshold, determines that the image is a low-resolution image. The thresholds in the above description may be set based on actual application requirements.

For blurred images, the embodiments of this application provide an exemplary detection algorithm for blurred images, in which Gaussian filtering is performed on an endoscopic image to eliminate moiré generated during endoscopic sampling, where the moiré refers to high-frequency interference fringes appearing on a photosensitive element, and is a kind of colored high-frequency irregular fringes appearing on the image. The Gaussian-filtered endoscopic image is defined as R. The Gaussian-filtered endoscopic image is then processed by median filtering. The median-filtered endoscopic image is defined as P. For example, the median filtering may be 3*3 median filtering. Gradients of the image P and the image R are calculated respectively, and images G_P and G_R are obtained using a pixel image edge detection operator. The pixel image edge detection operator may be a Sobel operator. A similarity between G_P and G_R is calculated, and it is determined whether the endoscopic image is a blurred image based on the similarity calculation result. A higher similarity between G_P and G_R indicates a more blurred endoscopic image, and a lower similarity between G_P and G_R indicates a clearer endoscopic image.

For images with abnormal hues and/or overexposure/underexposure, this application also provides an exemplary detection algorithm. Due to the various abnormalities such as abnormal hues and overexposure/underexposure, it is necessary to build a standard library file with qualified hue and normal shooting. During detection of an endoscopic image, first, the image is evenly divided into n image blocks, from which m image blocks are randomly selected, where m and n are both positive integers, and m<n. H, S, and V of the m image blocks are respectively calculated in an HSV (Hue, Saturation, Value) space, where H represents hue, and S represents saturation or color purity, and V represents luminance/brightness. The HSV space is mostly used in image processing. Then, using H and S as features, H and S of the m image blocks are matched against H and S of at least one standard image in the standard library file, and a corresponding similarity is calculated for each image block. In a possible situation, for an image block, if there is one standard image, a similarity value between the image block and the standard image is obtained as the similarity between the image block and the at least one standard image in the standard library file; if there are multiple standard images, an average value of similarities between the image block and the multiple standard images is obtained as the similarity between the image block and the at least one standard image in the standard file. A similarity threshold is set. If the number of image blocks whose similarity to the standard image reaches the similarity threshold in the m image blocks reaches a certain threshold, the endoscopic image is determined to be a matched image, that is, an image with normal hues and without overexposure/underexposure. Otherwise, if the number of image blocks whose similarity to the standard image reaches the similarity threshold in the m image blocks reaches the certain threshold, the endoscopic image is determined to be a non-matched image, that is, an image with abnormal hues and/or overexposure/underexposure. For example, the endoscopic image may be divided into 7*7 image blocks, and 9 image blocks may be randomly taken out for calculation of H, S, and V. Using H and S as features, similarities between the 9 image blocks and the standard image may be respectively calculated. If the number of images blocks that are matched successfully among the 9 image blocks is greater than or equal to 5, the endoscopic image is considered to be an image with normal hues and without overexposure/underexposure. If the number of images blocks that are matched successfully among the 9 image blocks is less than 5, the endoscopic image is considered to be an image with abnormal hues and/or overexposure/underexposure. The similarity threshold and the certain threshold for determining whether the image blocks are successfully matched may be set and adjusted based on actual application requirements, which is not limited in the embodiments of this application.

Optionally, the acquisition and determination of the image quality information may be performed before the operation status of the endoscope when capturing the endoscopic image is acquired, so as to ensure that the endoscopic images inputted to the image mode classification network are all high-quality images, to facilitate the determination made by the image mode classification network and improve the recognition precision of the image mode classification network. In other words, the step of acquiring the operation status of the endoscope when capturing the endoscopic image is performed in response to the image quality information satisfying an image quality threshold.

Step 330: Input the endoscopic image into a target region locating network to obtain region coordinates outputted by the target region locating network, in response to an image mode of the endoscopic image being an NBI mode, the target region locating network being a machine learning network obtained through training with second training images, and the second training images being each marked with a target region.

When the image mode of the endoscopic image captured by the endoscope that is acquired through step 320 indicates that the image is in the NBI mode, the endoscopic image is inputted into the target region locating network. If the image mode of the endoscopic image captured by the endoscope that is acquired through step 320 indicates that the image is in the white light mode, the step of inputting the endoscopic image into the target region locating network will not be performed.

The target region locating network is configured to locate the target region in the inputted endoscopic image in the NBI mode. For example, the target region may be a suspicious lesion region. When determining that there is a suspicious lesion region in the endoscopic image by using the target region locating network, the computer device may acquire and output location coordinates of the suspicious lesion region.

The target region locating network may be an end-to-end real-time target detection and recognition network. The target region locating network may be obtained in advance by training with a machine learning model.

For example, in the training process, the second training images marked with the target region may be inputted into the model training device to construct a target region locating network, a loss function may be calculated based on an output result of the target region locating network and coordinates of the target region, and parameters in the target region locating network may be adjusted according to the loss function, so that the output result of the target region locating network obtained by training is as close to the coordinates of the target region corresponding to the second training images with the target region as possible.

In a possible situation, the YOLO v2 algorithm may be used to locate and detect the target region. YOLO v2 uses a single neural network to transform the target detection problem into a regression problem of extracting bounding boxes and category probabilities in the image. YOLO v2 adopts the multi-scale training method and borrows the idea of Faster RCNN anchor box, which can improve the progress of model detection and generalization ability while ensuring the detection speed. When the YOLO v2 algorithm is applied to the lesion locating scenario of this application, the size of the anchor box may be obtained based on free training data clustering. During training of the target region locating network, first, initialization parameters of the target region locating network may be trained using Imagenet (image database) data, and then the initialization parameters of the target region locating network are adjusted using data in this field, so that the obtained target region locating network can perform well in this field. The Imagenet data is an open-source data set related to image classification and target detection in the computer vision field, covering thousands of categories in various fields, and with a million-level data volume. In the embodiments of this application, by training the initialization parameters of the obtained model by using the Imagenet data, the model can well converge to obtain a global optimal solution. On this basis, specific training is carried out for a specific field, so as to improve the determination precision of the model in the specific field. For example, the initialized model is further trained using endoscopic images in the medical field to obtain a model with higher precision in the medical field.

During the use of the target region locating network, the computer device may input an endoscopic image in the NBI mode into the target region locating network, and accordingly the target region locating network may output coordinates of the target region in the endoscopic image.

Step 340: Acquire an image corresponding to the region coordinates in the endoscopic image as the target region image.

Optionally, the coordinates of the target region may be coordinates of several vertexes of a polygon (such as a rectangle) that can frame the target region. After acquiring the corresponding region coordinates, the computer device can connect the coordinates of the vertexes in sequence to obtain a target region range, and acquire an image within this range as the target region image. In some implementations, the polygon may be a shape with four vertexes, which may not be necessarily as a rectangle. In some implementations, the polygon may be a shape with more than four vertexes, for example but not limited, five, six, seven, eight, ten vertexes.

Step 350: Input the target region image into a coding network to obtain a semantic feature of the target region image outputted by the coding network, the coding network being a network part configured to extract image features in an image classification network, and the image classification network being a machine learning network obtained through training with first training images and image categories of the first training images.

Based on the description of the coding network in the embodiment shown in FIG. 2, the coding network is configured to obtain the semantic feature of the target region image inputted to the coding network without the need to classify the target region image. During operation of the coding network, the coding network may perform dimensionality reduction processing on the target region image inputted to the coding network, and use data of the dimensionality-reduced target region image as an input to the database and the matching network for subsequent sample matching and comparison.

Figure 5:
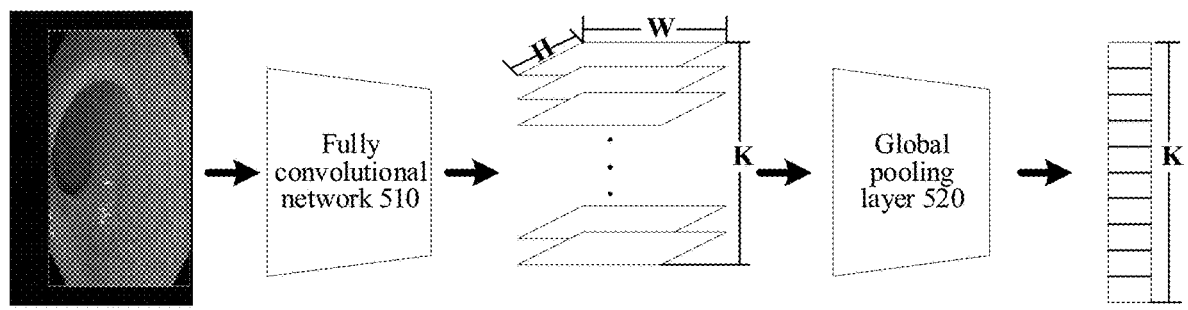
FIG. 5 is a schematic structural diagram of a coding network according to an exemplary embodiment of this application.

FIG. 5 is a schematic structural diagram of a coding network according to an exemplary embodiment of this application. As shown in FIG. 5, the coding network may include a fully convolutional network 510 and a global pooling layer 520. The fully convolutional network 510 is configured to parse the target region image inputted to the coding network into a high-dimensional semantic feature. The high-dimensional semantic feature may be expressed as a feature map of a size H*W*K, where H corresponds to the length of the feature map, W corresponds to the width of the feature map, and K corresponds to the number of feature maps. The feature map will be subsequently imported into the global pooling layer 520 for subsequent processing to reduce the dimensionality of the high-dimensional semantic feature, to obtain a 1*K-dimensional semantic feature vector, for subsequent matching of the semantic features. In some implementations, H, W, and/or K are positive integers.

Optionally, when the coding network acquires the semantic feature of the target region image, the database may preliminarily filter image samples stored in the database based on the semantic feature acquired by the coding network, so as to obtain samples whose semantic features are similar to the semantic feature of the target region image, thereby reducing meaningless matching in the subsequent matching process and alleviating the workload of the matching network. In some implementations, a number of the filtered image samples is much smaller than the image samples stored in the database, so as to have a smaller number of image samples for the subsequent matching process, thus reducing meaningless matching in the subsequent matching process and alleviating the workload of the matching network. In some other implementations, the filtered image samples may be referred as selected image samples because they are selected during the above filtering process wherein the database may preliminarily filter image samples stored in the database based on the semantic feature acquired by the coding network.

For example, the database can acquire the image type corresponding to the target region image, and select, by screening based on the image type, semantic features corresponding to the image samples of the same image type, so that subsequently the database only needs to match the semantic feature of the target region image against the selected semantic features corresponding to the image samples, and does not have to match the semantic feature of the target region image against the semantic features corresponding to all the image samples in the database. For example, the image type may indicate a type of an organ in the image, etc.

The database is configured to store a K-dimensional semantic feature corresponding to an original sample. In addition, in order to be able to trace back to the original image, the database also stores related information based on which the original image can be traced back. In order to realize preliminary filtering of the samples in the database based on the inputted target region image, the database has a special plan for the storage of K-dimensional semantic features. The K-dimensional semantic feature of the original sample stored in the database is obtained through the coding network that extracts the semantic feature from the target region image.

Step 360: Input the semantic feature of the target region image and the semantic features of the image samples into a matching network, and obtain matching scores between the target region image and the image samples outputted by the matching network, the matching network being obtained by training with semantic feature pairs each marked with a matching tag, each of the semantic feature pairs including semantic features of two images, and the matching tag being used for indicating whether the corresponding semantic feature pairs match.

Optionally, the matching network may be composed of a dual-input similarity measurement network (Siamese network) and configured to evaluate a matching relationship between two input samples inputted to the matching network. This matching relationship may be the degree of similarity between the two or may be a spatial distance between the two. During operation of the matching network, when a semantic feature of a target region image that needs to be retrieved is inputted to the matching network, the database also inputs semantic features of image samples of the corresponding type into the matching network, so that the matching network sequentially matches the semantic feature of the target region image against the semantic features of the image samples selected from the database. The matching network may output a matching result based on a degree of matching between the semantic feature of the target region image and the semantic feature of each image sample. The matching result may be a score of the matching relationship between the two, where the score of the matching relationship may be in various forms, such as Euclidean distance, cosine similarity, etc., which is not limited in this application.

In the training process of the matching network, the matching network may be trained by inputting semantic feature pairs each marked with a matching tag into the model training device. Each semantic feature pair may include two paired semantic features. The matching tag is used for indicating whether the corresponding semantic feature pair matches. That is to say, several semantic feature pairs and matching tags corresponding to the semantic feature pairs are inputted into the matching network. Then, the model training device calculates a loss function based on the output result of the matching network and the matching tag, and adjusts parameters in the matching network based on the calculation result of the loss function, so that the output result of the matching network obtained by training can indicate a result as close to the matching label as possible.

Figure 6:
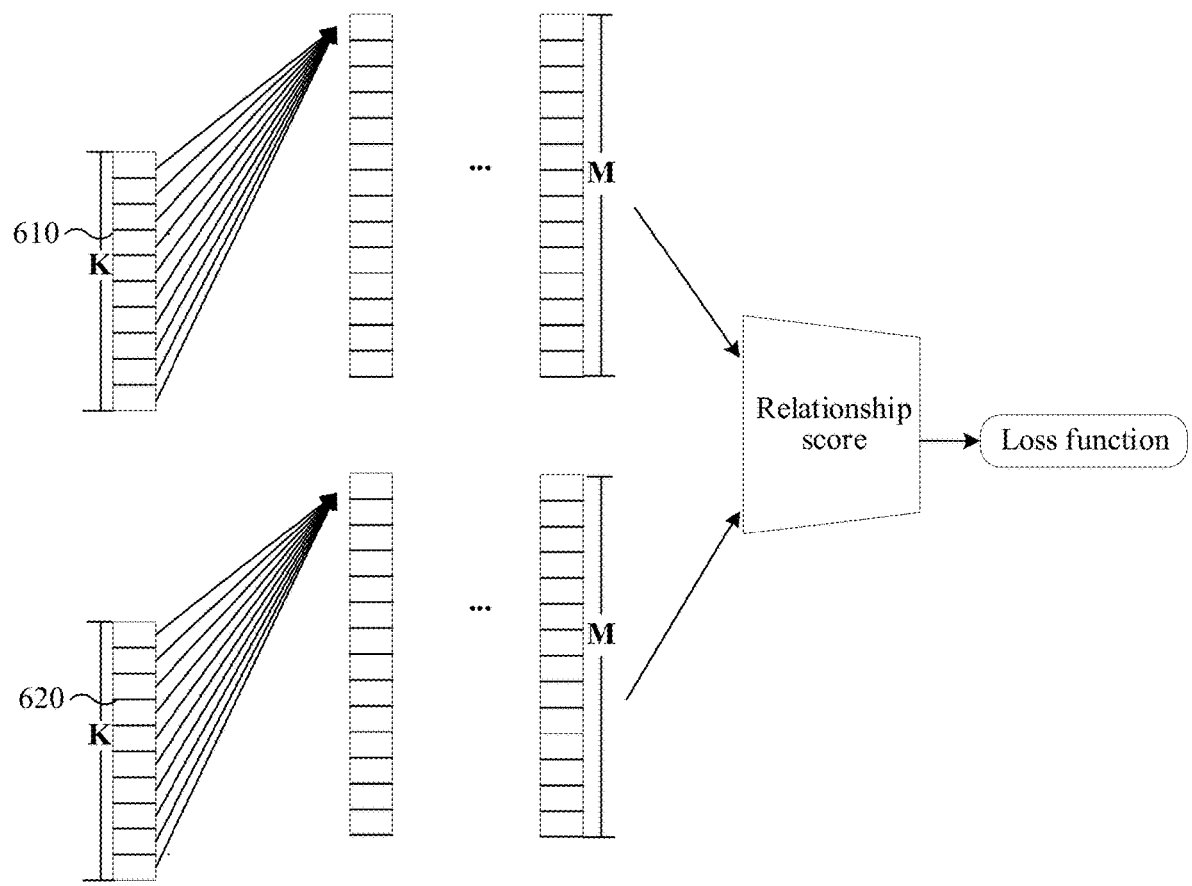
FIG. 6 is a schematic diagram showing training of a matching network according to an exemplary embodiment of this application.

In a possible case, FIG. 6 is a schematic diagram showing training of a matching network according to an exemplary embodiment of this application. As shown in FIG. 6, A K-dimensional semantic feature 610 of an endoscopic image 1 and a K-dimensional semantic feature 620 of an endoscopic image 2 are simultaneously inputted into the matching network, non-linearly changed to M dimensions by using multiple fully connected layers and activation functions, and calculates a relationship score, which is recorded as D, between the two. If the relationship score between the semantic feature of the target region image and the semantic feature of each image sample in the matching network is defined as a Euclidean distance, then the loss function may be defined as the following form:

$$(1-Y)\frac{1}{2}(D)^2 + Y\frac{1}{2}\{\max(0, \tau - D)\},$$

where, τ represents a smoothing parameter for suppressing the relationship score. When two samples are positively correlated, Y=0, or otherwise Y=1.

In some implementations, the closer the matching between the semantic features of the endoscopic image 1 and the endoscopic image 2 is, the smaller the D representing the relationship score is. In some other implementations, the larger a value of the relationship score is, the closer the matching between the semantic features of the endoscopic image 1 and the endoscopic image 2 is.

Step 370: Determine the target image sample based on the matching scores between the target region image and the image samples. In some implementations, the higher the matching score is, the closer the matching is.

Optionally, the computer device sorts the image samples in descending order of the corresponding matching scores, and uses top n image samples as the target image samples, wherein n≥1, and n is an integer; or the computer device uses the image sample with the corresponding matching score higher than a matching score threshold among the image samples as the target image sample; or the computer device sorts the image samples in descending order of the corresponding matching scores, and uses the image sample with the corresponding matching score higher than a matching score threshold among top n image samples as the target image sample.

In some other implementations, the computer device may sort the image samples in descending order of the corresponding matching scores, and using one of top n image samples as the target image sample, wherein n≥ 1 and n is an integer; or the computer device may use an image sample among the image samples with the corresponding matching score higher than a matching score threshold as the target image sample; or the computer device may sort the image samples in descending order of the corresponding matching scores, and using an image sample with the corresponding matching score higher than a matching score threshold among top n image samples as the target image sample.

The matching score between the target region image and each image sample is used for indicating the degree of similarity between the target region image and each image sample. For the acquisition of the target image sample, because a higher matching score indicates a higher degree of similarity between the target region image and the image sample, the computer device may sort the image samples in descending order of the corresponding matching scores. The higher an image sample is ranked, the higher the degree of similarity between the image sample and the target region image. Therefore, the top n image samples may be selected as the target image samples.

Alternatively, considering that one matching score may correspond to multiple image samples and the top n image samples may not include all the image samples corresponding to the top-ranked matching scores, the computer device may set a matching score threshold, and use all image samples whose matching scores are higher than the matching score threshold as the target image samples.

Alternatively, the computer device may first sort the image samples in descending order of the corresponding matching scores, and then screen the top n image samples based on a matching score threshold, so as to obtain image top-ranked image samples whose matching scores are higher than the matching score threshold.

Step 380: Acquire the matching result based on the target image sample.

Optionally, the matching result includes at least one of the following:

the target image sample;

the image category corresponding to the target image sample; and a matching degree between the target image sample and the target region image.

The computer device may acquire the target image sample based on the relevant information that is stored in the database and based on which the image sample can be traced back.

Step 390: Display the endoscopic image and the matching result in an endoscopic image display interface.

Optionally, in the endoscopic image display interface, a region mark is displayed corresponding to the endoscopic image, the region mark being used for indicating the target region in the endoscopic image.

Figure 7:
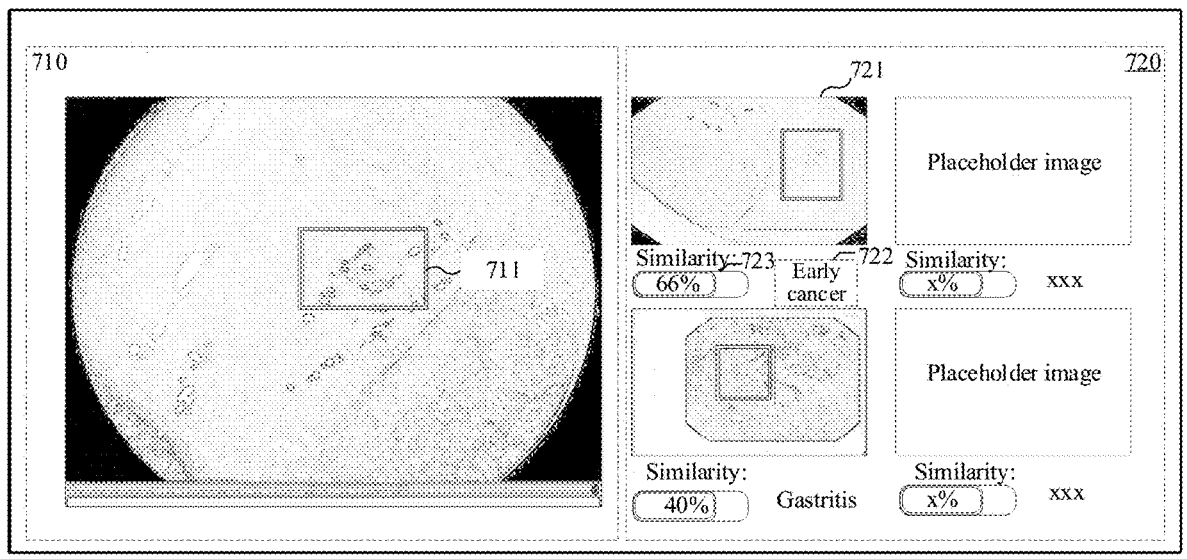
FIG. 7 is an interface diagram of an endoscopic image display interface according to an exemplary embodiment of this application.

FIG. 7 is an interface diagram of an endoscopic image display interface according to an exemplary embodiment of this application. As shown in FIG. 7, an endoscopic image is displayed in a region 710, a region mark 711 is displayed on the endoscopic image, and a matching result is displayed in a region 720. The matching result may include a target image sample 721, an image category 722 of the target image sample, and a matching degree 723 between the target image sample and the target region image. In some implementations, a matching score may be represented as a matching degree, which is a percentage ranging from 0% to 100%, inclusive.

Optionally, at the region mark 711 in the endoscopic image, the relevant information of the target image sample corresponding to the highest matching degrees in the matching result may be correspondingly displayed. The relevant information is, for example, the image category corresponding to the target image sample and the degree of matching between the target image sample and the endoscopic image.

Based on the above, with the endoscopic image display method provided by this application, by acquiring an endoscopic image captured by an endoscope, locating a target region image in the endoscopic image, inputting the target region image into a coding network to obtain a semantic feature of the target region image outputted by the coding network, matching the semantic feature of the target region image against semantic features of image samples to obtain a matching result, displaying the endoscopic image and the matching result in an endoscopic image display interface, the accuracy of diagnosis with the assistance of the endoscope is improved by localizing and matching the image of the lesion in the endoscopic image during the use of the endoscope.

Figure 8:
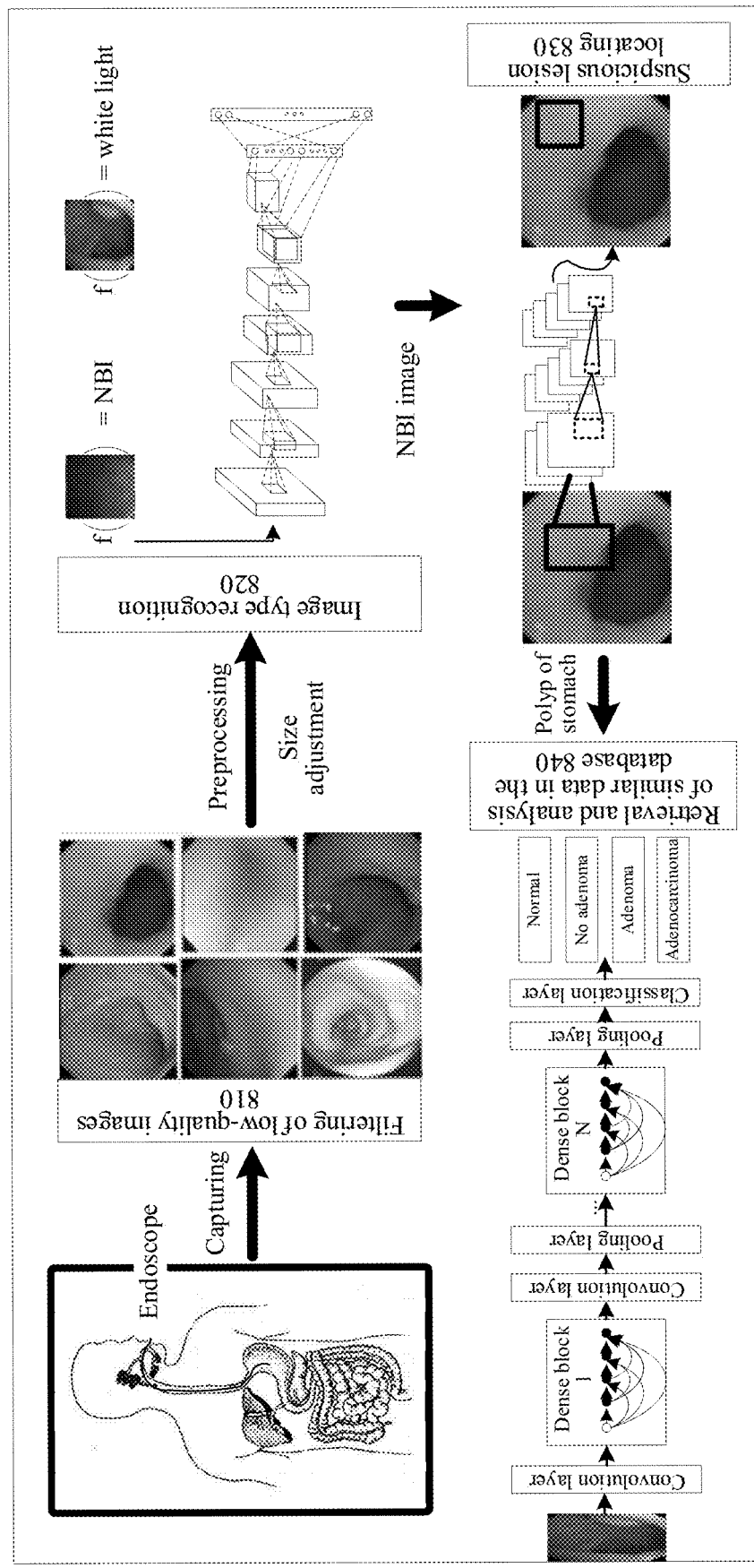
FIG. 8 is a schematic diagram showing an endoscopic image recognition process according to an exemplary embodiment of this application.

FIG. 8 is a schematic diagram showing an endoscopic image recognition process according to an exemplary embodiment of this application. As shown in FIG. 8, for example, when the object examined by the endoscope is the stomach, a user inserts the endoscope into the stomach of the human body through the natural orifice of the human body or a small incision made by surgery, captures endoscopic images, and inputs the captured endoscopic images into the computer device. Since there may be food residues in the stomach or other factors that may affect the image quality of the endoscopic images, it is necessary to filter out low-quality image 810 from the endoscopic images by using a computer device to select high-quality endoscopic images for subsequent processing. The computer device pre-processes the selected high-quality endoscopic images, adjusts the image size to a size that meets the requirements of the image mode classification network, and then starts image type recognition 820. The process of image type recognition can rely on the image mode classification network to select, by screening, an endoscopic image of the NBI mode from the endoscopic images inputted to the image mode classification network, and locate a suspicious lesion 830 in the endoscopic image of the NBI mode. The process of suspicious lesion locating can rely on the target region locating network to locate a suspicious lesion in the endoscopic image inputted to the target region locating network, and acquire region coordinates of a lesion region corresponding to the suspicious lesion. Retrieval and analysis of similar data in the database 840 is performed for the suspicious lesion region. This process can rely on the coding network and the matching network to encode the inputted endoscopic image to obtain a semantic feature of the endoscopic image, and match the semantic feature against semantic features of the sample images that are stored in the database and have been preliminarily screened to obtain sample images that match the image of the suspicious lesion region, so as to obtain relevant information of the suspicious lesion, such as the type of the lesion, the degree of matching with the sample image, etc.

Figure 9:
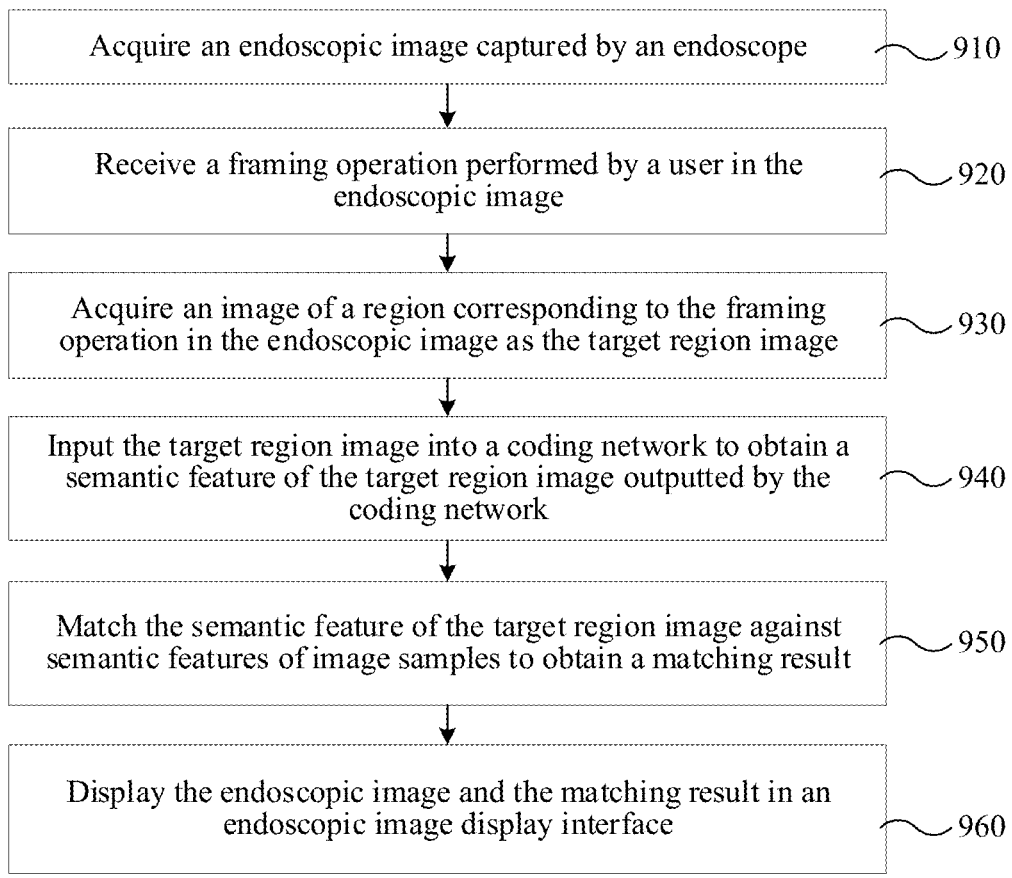
FIG. 9 is a flowchart of an endoscopic image display method according to an exemplary embodiment of this application.

Based on the endoscopic image display method shown in FIG. 2 or FIG. 3, when the step of locating the target region image in the endoscopic image is performed by the user, refer to FIG. 9, which is a flowchart of an endoscopic image display method according to an exemplary embodiment of the present application. The endoscopic image display method can be used in a computer device, such as the image recognition device shown in FIG. 1 described above. As shown in FIG. 9, the endoscopic image display method may include the following steps:

Step 910: Acquire an endoscopic image captured by an endoscope.

Optionally, when the endoscope captures the endoscopic image, the endoscopic image may be displayed in the endoscopic image display interface in real time. In the endoscopic image display interface, the user may perform a user operation in the endoscopic image in the endoscopic image display interface.

Optionally, the user operation may include, but is not limited to, a zoom-in operation, a zoom-out operation, and a framing (select) operation.

The computer device may acquire the endoscopic image captured by the endoscope, and may also acquire the user operation performed by the user through the interface interaction.

Step 920: Receive a framing operation performed by a user in the endoscopic image.

The framing operation performed by the user in the endoscopic image may be an operation of selecting a partial region in the endoscopic image by the user through an external device such as a mouse, or may be an operation of directly interacting with the endoscopic image display interface by the user to select a partial region in the endoscopic image display interface.

Step 930: Acquire an image of a region corresponding to the framing operation in the endoscopic image as the target region image.

In response to the user performing a framing operation in the endoscopic image display interface, a framing box may be displayed in a region on which the framing operation acts to indicate that this region is a framed region, and an image within the framed region is acquired as the target region image.

Optionally, in the NBI mode, the user may perform a framing operation, or, in the NBI mode, the image corresponding to the framed region may be acquired as the target region image.

Optionally, after the user acquires the target region image by performing the framing operation, image quality information of the target region image may be acquired, the image quality information including at least one of degree of blurring, exposure and hue abnormality, or effective resolution.

In response to the image quality information meeting an image quality threshold, the computer device executes the step of inputting the target region image into the coding network, so that the target region image processed by the coding network is the target region image with high image quality, thereby reducing the impact of low-quality images on the subsequent recognition and matching processes and avoiding unnecessary workload.

For the process of acquiring the image quality information of the target region image and determining whether the image quality information meets the image quality threshold, reference may be made to the related description of the process of obtaining the image quality information of the endoscopic image in the embodiment of FIG. 3, so the details will not be repeated here.

Step 940: Input the target region image into a coding network to obtain a semantic feature of the target region image outputted by the coding network, the coding network being a network part configured to extract image features in an image classification network, and the image classification network being a machine learning network obtained through training with first training images and image categories of the first training images.

Step 950: Match the semantic feature of the target region image against semantic features of image samples to obtain a matching result, the matching result being used for indicating a target image sample that matches the target region image among the image samples.

Figure 10:
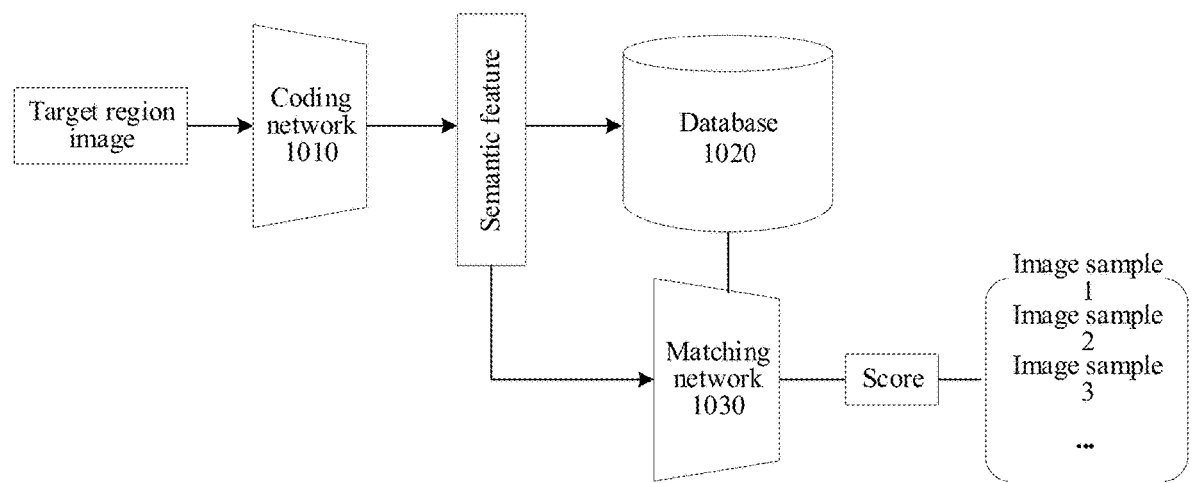
FIG. 10 is a schematic diagram of an endoscopic image retrieval system according to an exemplary embodiment of this application.

FIG. 10 is a schematic diagram of an endoscopic image retrieval system according to an exemplary embodiment of this application. As shown in FIG. 10, the endoscopic image retrieval system may include a coding network 1010, a database 1020, and a matching network 1030. When a target region image is inputted to the endoscopic image retrieval system, the endoscopic image is first processed by the coding network 1010 to obtain a K-dimensional semantic feature corresponding to the endoscopic image, and the K-dimensional semantic feature is used as an input to the database 1020 and the matching network 1030. The K-dimensional semantic feature being obtained by performing dimensionality reduction on the semantic feature. The database 1020 preliminarily screens image samples in the database based on the K-dimensional semantic feature to obtain semantic features of the image samples that are close to the semantic feature of the endoscopic image, and inputs the semantic features of the image samples to the matching network 1030. The matching network 1030 matches the semantic feature of the endoscopic image inputted from the coding network 1010 against the semantic features of the image samples inputted from the database 1020, and scores a matching relationship between the semantic feature of the endoscopic image and the semantic feature of each image sample to obtain a scoring result. The computer device may sort the scoring results in descending order of score values, and acquire the target image samples from the image samples corresponding to the semantic feature of the endoscopic image inputted from the database 1020 according to a certain determination rule.

Step 960: Display the endoscopic image and the matching result in an endoscopic image display interface.

The endoscopic image displayed in the endoscopic image display interface is the endoscopic image corresponding to the framing operation performed by the user, and the matching result refers to a matching result corresponding to the image in the framed region selected by the framing operation of the user.

Based on the above, with the endoscopic image display method provided by this application, by acquiring an endoscopic image captured by an endoscope, locating a target region image in the endoscopic image, inputting the target region image into a coding network to obtain a semantic feature of the target region image outputted by the coding network, matching the semantic feature of the target region image against semantic features of image samples to obtain a matching result, and displaying the endoscopic image and the matching result in an endoscopic image display interface, the accuracy of diagnosis with the assistance of the endoscope is improved by localizing and matching the image of the lesion in the endoscopic image during the use of the endoscope.

Figure 11:
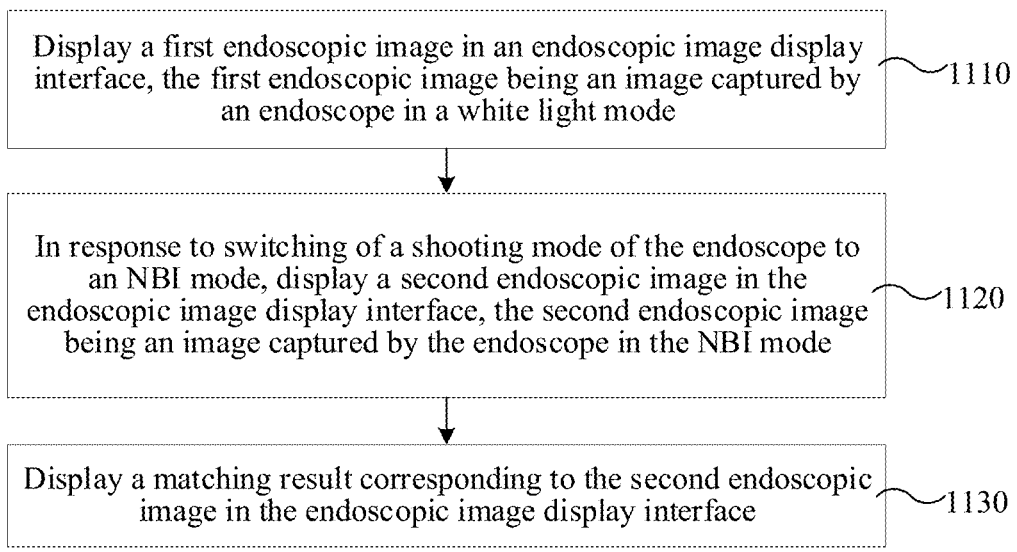
FIG. 11 is a flowchart of an endoscopic image display method according to an exemplary embodiment of this application.

FIG. 11 is a flowchart of an endoscopic image display method according to an exemplary embodiment of this application. The endoscopic image display method may be applied in a computer device, for example, the image display apparatus shown in FIG. 1. As shown in FIG. 11, the endoscopic image display method may include the following steps:

Step 1111: Display a first endoscopic image in an endoscopic image display interface, the first endoscopic image being an image captured by an endoscope in a white light mode.

During the use of the endoscope, the user first uses the endoscope to capture an image of an organ in the white light mode to obtain a global image of the organ. When finding that there is a suspicious lesion region in the image captured by the endoscope, the user may switch the shooting mode of the endoscope to the NBI mode. In the NBI mode, the user can observe the distribution of blood vessels, and blood appears as black in the image captured in the NBI mode. In the NBI mode, the morphology of the mucosal epithelium of the digestive tract can also accurately shown, to facilitate the observation and diagnosis of the lesion region by the user.

Step 1120: In response to switching of a shooting mode of the endoscope to a narrow band imaging (NBI) mode, display a second endoscopic image in the endoscopic image display interface, the second endoscopic image being an image captured by the endoscope in the NBI mode.

Step 1130: Display a matching result corresponding to the second endoscopic image in the endoscopic image display interface, the matching result being used for indicating a target image sample that matches a target region image in the second endoscopic image.

The matching result corresponding to the second endoscopic image is the target image sample matching the second endoscopic image and other related information that are obtained after the image recognition device performs recognition and matching on the second endoscopic image. For the process of recognizing the second endoscopic image by the computer device, reference may be made to the relevant content in the endoscopic image display method shown in any of the embodiments of FIG. 2, FIG. 3, and FIG. 8.

Based on the above, with the endoscopic image display method provided by this application, by displaying, in an endoscopic image display interface, an image captured by an endoscope in a white light mode, displaying, in response to switching of a shooting mode of the endoscope to an NBI mode, an image captured by the endoscope in the NBI mode in the endoscopic image display interface, and displaying a matching result corresponding to the second endoscopic image in the endoscopic image display interface, i.e., by localizing and matching the image of the lesion in the endoscopic image, the accuracy of diagnosis with the assistance of the endoscope is improved.

Figure 12:
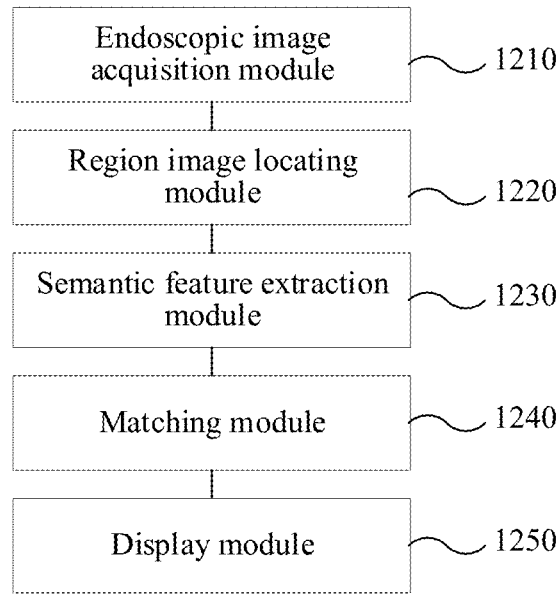
FIG. 12 is a structural block diagram of an endoscopic image display apparatus according to an exemplary embodiment.

FIG. 12 is a structural block diagram of an endoscopic image display apparatus according to an exemplary embodiment. The endoscopic image display apparatus may be used in a computer device. For example, the computer device may be the image recognition device shown in FIG. 1 to perform all or part of the steps of the method shown in any of the embodiments in FIG. 2, FIG. 3, and FIG. 9. As shown in FIG. 12, the endoscopic image display apparatus may include:

an endoscopic image acquisition module 1210, configured to acquire an endoscopic image captured by an endoscope;

a region image localizing module 1220, configured to locate a target region image in the endoscopic image, the target region image being a partial image including a target region in the endoscopic image;

a semantic feature extraction module 1230, configured to input the target region image into a coding network to obtain a semantic feature of the target region image outputted by the coding network, the coding network being a network part configured to extract image features in an image classification network, and the image classification network being a machine learning network obtained through training with first training images and image categories of the first training images;

a matching module 1240, configured to match the semantic feature of the target region image against semantic features of image samples to obtain a matching result, the matching result being used for indicating a target image sample that matches the target region image among the image samples.

a display module 1250, configured to display the endoscopic image and the matching result in an endoscopic image display interface.

Optionally, the matching module 1240 includes:

a matching score acquisition sub-module, configured to input the semantic feature of the target region image and the semantic features of the image samples into a matching network, and obtain matching scores between the target region image and the image samples outputted by the matching network, the matching network being obtained by training with semantic feature pairs each marked with a matching tag, each of the semantic feature pairs including semantic features of two images, and the matching tag being used for indicating whether the corresponding semantic feature pairs match;

an image sample determination sub-module, configured to determine the target image sample based on the matching scores between the target region image and the image samples; and a matching result acquisition sub-module, configured to acquire the matching result based on the target image sample.

Optionally, the image sample determination sub-module 1220 is configured to:

sort the image samples in descending order of the corresponding matching scores, and use top n image samples as the target image samples, wherein n≥1, and n is an integer; or use the image sample with the corresponding matching score higher than a matching score threshold among the image samples as the target image sample; or sort the image samples in descending order of the corresponding matching scores, and use the image sample with the corresponding matching score higher than a matching score threshold among top n image samples as the target image sample, wherein n≥1, and n is an integer.

Optionally, the matching result includes at least one of the following:

the target image sample;

the image category corresponding to the target image sample; and a matching degree between the target image sample and the target region image.

Optionally, the apparatus further includes:

a second display module, configured to display a region mark corresponding to the endoscopic image in the endoscopic image display interface, the region mark being used for indicating the target region in the endoscopic image.

Optionally, the region image localizing module 1220 includes:

a region coordinate acquisition sub-module, configured to input the endoscopic image into a target region locating network to obtain region coordinates outputted by the target region locating network, the target region locating network being a machine learning network obtained through training with second training images, and the second training images being each marked with a target region; and a first region image acquisition sub-module, configured to acquire an image corresponding to the region coordinates in the endoscopic image as the target region image.

Optionally, the region image localizing module 1220 includes:

a user operation receiving sub-module, configured to receive a framing operation performed by a user in the endoscopic image; and a second region image acquisition sub-module, configured to acquire an image of a region corresponding to the framing operation in the endoscopic image as the target region image.

Optionally, the region image localizing module 1220 is configured to perform the operation of locating a target region image in the endoscopic image, in response to an image mode of the endoscopic image being a narrow band imaging (NBI) mode.

Optionally, the apparatus further includes:

an image mode information acquisition module, configured to input the endoscopic image into an image mode classification network, and obtaining image mode information outputted by the image mode classification network, the image mode classification network being a machine learning network obtained through training with third training images, each of the third training images being marked with an image mode, and the image mode information being used for indicating whether the image mode of the endoscopic image is the NBI mode.

Optionally, the apparatus further includes:

an operation status acquisition module, configured to acquire an operation status of the endoscope during the capturing of the endoscopic image; and determine that the image mode of the endoscopic image is the NBI mode, in response to the operation status being the NBI state.

Optionally, the apparatus further includes:

an image quality information acquisition module, configured to acquire image quality information of the endoscopic image, the image quality information including at least one of degree of blurring, exposure and hue abnormality, or effective resolution; and a regional image positioning module 1220, configured to perform the operation of locating a target region image in the endoscopic image, in response to the image quality information satisfying an image quality threshold.

Based on the above, the endoscopic image display apparatus provided by this application is applied in a computer device, and by acquiring an endoscopic image captured by an endoscope, locating a target region image in the endoscopic image, inputting the target region image into a coding network to obtain a semantic feature of the target region image outputted by the coding network, matching the semantic feature of the target region image against semantic features of image samples to obtain a matching result, and displaying the endoscopic image and the matching result in an endoscopic image display interface, the accuracy of diagnosis with the assistance of the endoscope is improved by localizing and matching the image of the lesion in the endoscopic image during the use of the endoscope.

Figure 13:
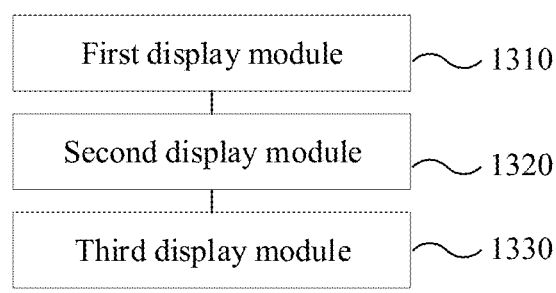
FIG. 13 is a structural block diagram of an endoscopic image display apparatus according to an exemplary embodiment.

FIG. 13 is a structural block diagram of an endoscopic image display apparatus according to an exemplary embodiment. The endoscopic image display apparatus may be used in a computer device. For example, the computer device may be the image display apparatus shown in FIG. 1 to perform all or part of the steps of the method shown in FIG. 11. As shown in FIG. 13, the endoscopic image display apparatus may include:

a first display module 1310, configured to display a first endoscopic image in an endoscopic image display interface, the first endoscopic image being an image captured by an endoscope in a white light mode;

a second display module 1320, configured to, in response to switching of a shooting mode of the endoscope to a narrow band imaging (NBI) mode, display a second endoscopic image in the endoscopic image display interface, the second endoscopic image being an image captured by the endoscope in the NBI mode; and a third display module 1330, configured to display a matching result corresponding to the second endoscopic image in the endoscopic image display interface, the matching result being used for indicating a target image sample that matches a target region image in the second endoscopic image.

Based on the above, the endoscopic image display apparatus provided by this application is applied in a computer device, and by displaying, in an endoscopic image display interface, an image captured by an endoscope in a white light mode, displaying, in response to switching of a shooting mode of the endoscope to an NBI mode, an image captured by the endoscope in the NBI mode in the endoscopic image display interface, and displaying a matching result corresponding to the second endoscopic image in the endoscopic image display interface, i.e., by localizing and matching the image of the lesion in the endoscopic image, the accuracy of diagnosis with the assistance of the endoscope is improved.

Figure 14:
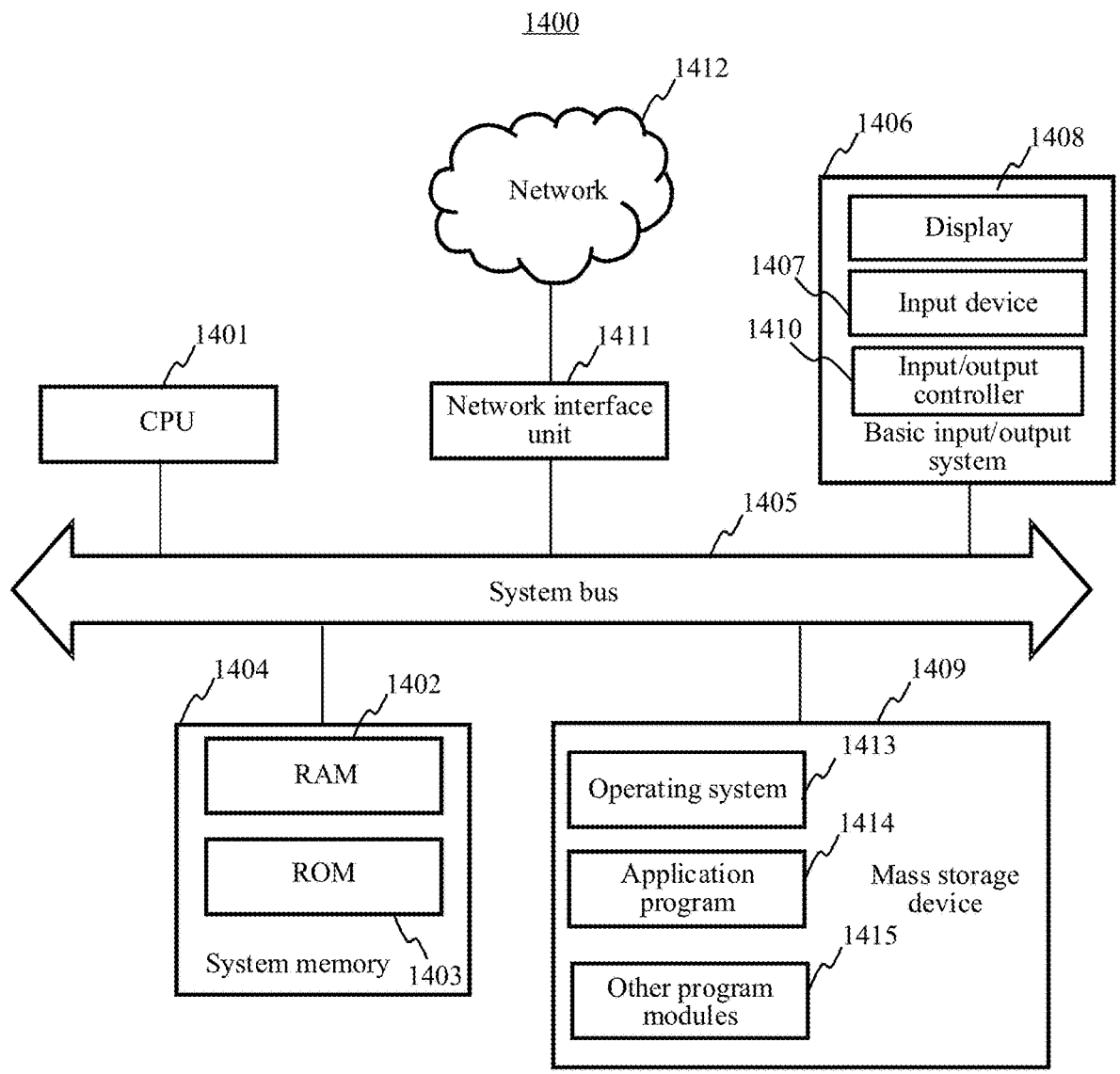
FIG. 14 is a structural block diagram of a computer device according to an exemplary embodiment.

FIG. 14 is a structural block diagram of a computer device 1400 according to an exemplary embodiment. The computer device may be implemented as the image recognition device or the image display apparatus in the above solutions of this application. The computer device 1400 includes a central processing unit (CPU) 1401, a system memory 1404 including a random-access memory (RAM) 1402 and a read-only memory (ROM) 1403, and a system bus 1405 connecting the system memory 1404 to the CPU 1401. The computer device 1400 further includes a basic input/output system (I/O system) 1406 configured to transmit information between components in the computer, and a mass storage device 1409 configured to store an operating system 1413, an application 1414, and another program module 1415.

The basic I/O system 1406 includes a display 1408 configured to display information and an input device 1407 such as a mouse or a keyboard that is configured for information inputting by a user. The display 1408 and the input device 1407 are both connected to the CPU 1401 by an input/output controller 1410 connected to the system bus 1405. The basic I/O system 1406 may further include the input/output controller 1410, to receive and process inputs from a plurality of other devices, such as a keyboard, a mouse, or an electronic stylus. Similarly, the input/output controller 1410 further provides an output to a display screen, a printer, or other type of output device.

The mass storage device 1409 is connected to the CPU 1401 through a mass storage controller (not shown) connected to the system bus 1405. The mass storage device 1409 and an associated computer-readable medium provide non-volatile storage for the computer device 1400. That is, the mass storage device 1409 may include a computer-readable medium (not shown) such as a hard disk or a compact disc ROM (CD-ROM) drive.

In various embodiments in the present disclosure, a unit may refer to a software unit, a hardware unit, or a combination thereof. A software unit may include a computer program or part of the computer program that has a predefined function and works together with other related parts to achieve a predefined goal, such as those functions described in this disclosure. A hardware unit may be implemented using processing circuitry and/or memory configured to perform the functions described in this disclosure. Each unit can be implemented using one or more processors (or processors and memory). Likewise, a processor (or processors and memory) can be used to implement one or more units. Moreover, each unit can be part of an overall unit that includes the functionalities of the unit. The description here also applies to the term unit and other equivalent terms.

In various embodiments in the present disclosure, a module may refer to a software module, a hardware module, or a combination thereof. A software module may include a computer program or part of the computer program that has a predefined function and works together with other related parts to achieve a predefined goal, such as those functions described in this disclosure. A hardware module may be implemented using processing circuitry and/or memory configured to perform the functions described in this disclosure. Each module can be implemented using one or more processors (or processors and memory). Likewise, a processor (or processors and memory) can be used to implement one or more modules. Moreover, each module can be part of an overall module that includes the functionalities of the module. The description here also applies to the term module and other equivalent terms.

Without loss of generality, the computer-readable medium may include a computer storage medium and a communication medium. The computer storage medium includes volatile and non-volatile, removable and non-removable media that are configured to store information such as computer-readable instructions, data structures, program modules, or other data and that are implemented by using any method or technology. The computer storage medium includes a RAM, a ROM, an erasable programmable ROM (EPROM), an electrically erasable programmable ROM (EEPROM), a flash memory or another solid-state memory technology, a CD-ROM, a digital versatile disc (DVD) or another optical memory, a magnetic cassette, a magnetic tape, a magnetic disk memory, or another magnetic storage device. Certainly, those skilled in the art may learn that the computer storage medium is not limited to the above. The system memory 1404 and the mass storage device 1409 may be collectively referred to as a memory.

According to the embodiments of this application, the computer device 1400 may further be connected, through a network such as the Internet, to a remote computer on the network. That is, the computer device 1400 may be connected to a network 1412 by using a network interface unit 1411 connected to the system bus 1405, or may be connected to another type of network or a remote computer system (not shown) by using a network interface unit 1411.

The memory further includes one or more programs. The one or more programs are stored in the memory. The CPU 1401 executes the one or more programs to implement all or some steps of the method shown in FIG. 2, FIG. 3, FIG. 9, or FIG. 11.

A person skilled in the art is to be aware that in the one or more examples, the functions described in the embodiments of this application may be implemented by using hardware, software, firmware, or any combination thereof. When implemented by using software, the functions can be stored in a computer-readable medium or can be used as one or more instructions or code in a computer-readable medium for transferring. The computer-readable medium includes a computer storage medium and a communication medium, where the communication medium includes any medium that enables a computer program to be transmitted from one place to another. The storage medium may be any available medium accessible to a general-purpose or dedicated computer.

The embodiments of this application further provide a computer-readable storage medium, storing at least one instruction, at least one program, a code set, or an instruction set, the at least one instruction, the at least one program, the code set, or the instruction set being loaded and executed by a processor to perform the endoscopic image display method described above. For example, the computer-readable storage medium may be a ROM, a RAM, a CD-ROM, a magnetic tape, a floppy disk, and an optical data storage device.

Other embodiments of this application will be apparent to a person skilled in the art from consideration of the specification and practice of the disclosure here. This application is intended to cover any variations, uses or adaptive changes of this application following the general principles of this application, and includes the well-known knowledge and conventional technical means in the art and undisclosed in this application. The specification and the embodiments are considered as merely exemplary, and the scope and spirit of this application are pointed out in the following claims.

It is to be understood that this application is not limited to the precise structures described above and shown in the accompanying drawings, and various modifications and changes can be made without departing from the scope of this application. The scope of this application is described by the appended claims.

What is claimed is:

1. A method for displaying an endoscopic image, the method comprising:
   acquiring, by a device comprising a memory storing instructions and a processor in communication with the memory, an endoscopic image captured by an endoscope;
   locating, by the device, a target region image in the endoscopic image, the target region image being a partial image comprising a target region in the endoscopic image;
   inputting, by the device, the target region image into a coding network to obtain a semantic feature of the target region image, the coding network being a part of an image classification network, the coding network configured to extract image features, and the image classification network being a machine learning network obtained through training with first training images;
   matching, by the device, the semantic feature of the target region image against semantic features of image samples to obtain a matching result, the matching result indicating a target image sample that matches the target region image among the image samples; and
   displaying, by the device, the endoscopic image and the matching result in an endoscopic image display interface,
   wherein before the locating the target region image in the endoscopic image, the method further comprises:
   inputting the endoscopic image into an image mode classification network to obtain image mode information, the image mode classification network being a machine learning network obtained through training with third training images, each of the third training images being marked with an image mode, and the image mode information indicating whether the image mode of the endoscopic image is a narrow band imaging (NBI) mode.

2. The method according to claim 1, wherein the matching the semantic feature of the target region image against the semantic features of the image samples to obtain the matching result comprises:
   inputting the semantic feature of the target region image and the semantic features of the image samples into a matching network to obtain matching scores between the target region image and the image samples, the matching network being obtained by training with semantic feature pairs, each of the semantic feature pairs marked with a matching tag, each of the semantic feature pairs comprising semantic features of two images, and the matching tag indicating whether the corresponding semantic feature pairs match; and
   determining the target image sample among the image samples based on the matching scores; and
   acquiring the matching result based on the target image sample.

3. The method according to claim 2, wherein the determining the target image sample among the image samples based on the matching scores comprises:
   sorting the image samples in descending order of the corresponding matching scores, and using one of top n image samples as the target image sample, wherein n≥1 and n is an integer; or
   using an image sample among the image samples with the corresponding matching score higher than a matching score threshold as the target image sample; or
   sorting the image samples in descending order of the corresponding matching scores, and using an image sample with the corresponding matching score higher than a matching score threshold among top n image samples as the target image sample.

4. The method according to claim 1, wherein the matching result comprises at least one of the following:
   the target image sample;
   an image category corresponding to the target image sample; or
   a matching degree between the target image sample and the target region image.

5. The method according to claim 1, wherein the locating the target region image in the endoscopic image comprises:
   inputting the endoscopic image into a target region locating network to obtain region coordinates, the target region locating network being a machine learning network obtained through training with second training images, and each of the second training images marked with a target region; and
   acquiring an image corresponding to the region coordinates in the endoscopic image as the target region image.

6. The method according to claim 1, wherein before the locating a target region image in the endoscopic image, the method further comprises:
   acquiring an operation status of the endoscope during the capturing of the endoscopic image;
   determining whether the operation status is an NBI state; and
   in response to determining that the operation status is the NBI state, determining that the image mode of the endoscopic image is the NBI mode.

7. An apparatus for displaying an endoscopic image, the apparatus comprising:
   a memory storing instructions; and
   a processor in communication with the memory, wherein, when the processor executes the instructions, the processor is configured to cause the apparatus to perform:
      acquiring an endoscopic image captured by an endoscope;
      locating a target region image in the endoscopic image, the target region image being a partial image comprising a target region in the endoscopic image;
      inputting the target region image into a coding network to obtain a semantic feature of the target region image, the coding network being a part of an image classification network, the coding network configured to extract image features, and the image classification network being a machine learning network obtained through training with first training images;
      matching the semantic feature of the target region image against semantic features of image samples to obtain a matching result, the matching result indicating a target image sample that matches the target region image among the image samples; and displaying the endoscopic image and the matching result in an endoscopic image display interface, wherein, before the processor is configured to cause the apparatus to perform locating the target region image in the endoscopic image, the processor is configured to cause the apparatus to perform:

inputting the endoscopic image into an image mode classification network to obtain image mode information, the image mode classification network being a machine learning network obtained through training with third training images, each of the third training images being marked with an image mode, and the image mode information indicating whether the image mode of the endoscopic image is a narrow band imaging (NBI) mode.

8. The apparatus according to claim 7, wherein, when the processor is configured to cause the apparatus to perform matching the semantic feature of the target region image against the semantic features of the image samples to obtain the matching result, the processor is configured to cause the apparatus to perform:

inputting the semantic feature of the target region image and the semantic features of the image samples into a matching network to obtain matching scores between the target region image and the image samples, the matching network being obtained by training with semantic feature pairs, each of the semantic feature pairs marked with a matching tag, each of the semantic feature pairs comprising semantic features of two images, and the matching tag indicating whether the corresponding semantic feature pairs match; and determining the target image sample among the image samples based on the matching scores; and acquiring the matching result based on the target image sample.

9. The apparatus according to claim 8, wherein, when the processor is configured to cause the apparatus to perform determining the target image sample among the image samples based on the matching scores, the processor is configured to cause the apparatus to perform:

sorting the image samples in descending order of the corresponding matching scores, and using one of top n image samples as the target image sample, wherein n≥1 and n is an integer; or using an image sample among the image samples with the corresponding matching score higher than a matching score threshold as the target image sample; or sorting the image samples in descending order of the corresponding matching scores, and using an image sample with the corresponding matching score higher than a matching score threshold among top n image samples as the target image sample.

10. The apparatus according to claim 7, wherein the matching result comprises at least one of the following:

the target image sample;

an image category corresponding to the target image sample; or a matching degree between the target image sample and the target region image.

11. The apparatus according to claim 7, wherein, when the processor is configured to cause the apparatus to perform locating the target region image in the endoscopic image, the processor is configured to cause the apparatus to perform:

inputting the endoscopic image into a target region locating network to obtain region coordinates, the target region locating network being a machine learning network obtained through training with second training images, and each of the second training images marked with a target region; and acquiring an image corresponding to the region coordinates in the endoscopic image as the target region image.

12. The apparatus according to claim 7, wherein, before the processor is configured to cause the apparatus to perform locating a target region image in the endoscopic image, the processor is configured to cause the apparatus to perform:

acquiring an operation status of the endoscope during the capturing of the endoscopic image;

determining whether the operation status is an NBI state; and in response to determining that the operation status is the NBI state, determining that the image mode of the endoscopic image is the NBI mode.

13. A non-transitory computer-readable storage medium, storing computer-readable instructions, wherein, the computer-readable instructions, when executed by a processor, are configured to cause the processor to perform:

acquiring an endoscopic image captured by an endoscope;

locating a target region image in the endoscopic image, the target region image being a partial image comprising a target region in the endoscopic image;

inputting the target region image into a coding network to obtain a semantic feature of the target region image, the coding network being a part of an image classification network, the coding network configured to extract image features, and the image classification network being a machine learning network obtained through training with first training images;

matching the semantic feature of the target region image against semantic features of image samples to obtain a matching result, the matching result indicating a target image sample that matches the target region image among the image samples; and displaying the endoscopic image and the matching result in an endoscopic image display interface, wherein, before the computer-readable instructions are configured to cause the processor to perform locating the target region image in the endoscopic image, the computer-readable instructions are configured to cause the processor to perform:

inputting the endoscopic image into an image mode classification network to obtain image mode information, the image mode classification network being a machine learning network obtained through training with third training images, each of the third training images being marked with an image mode, and the image mode information indicating whether the image mode of the endoscopic image is a narrow band imaging (NBI) mode.

14. The non-transitory computer-readable storage medium according to claim 13, wherein, when the computer-readable instructions are configured to cause the processor to perform matching the semantic feature of the target region image against the semantic features of the image samples to obtain the matching result, the computer-readable instructions are configured to cause the processor to perform:

inputting the semantic feature of the target region image and the semantic features of the image samples into a matching network to obtain matching scores between the target region image and the image samples, the matching network being obtained by training with semantic feature pairs, each of the semantic feature pairs marked with a matching tag, each of the semantic feature pairs comprising semantic features of two images, and the matching tag indicating whether the corresponding semantic feature pairs match; and determining the target image sample among the image samples based on the matching scores; and acquiring the matching result based on the target image sample.

15. The non-transitory computer-readable storage medium according to claim 14, wherein, when the computer-readable instructions are configured to cause the processor to perform determining the target image sample among the image samples based on the matching scores, the computer-readable instructions are configured to cause the processor to perform:

sorting the image samples in descending order of the corresponding matching scores, and using one of top n image samples as the target image sample, wherein n≥1 and n is an integer; or using an image sample among the image samples with the corresponding matching score higher than a matching score threshold as the target image sample; or sorting the image samples in descending order of the corresponding matching scores, and using an image sample with the corresponding matching score higher than a matching score threshold among top n image samples as the target image sample.

16. The non-transitory computer-readable storage medium according to claim 13, wherein the matching result comprises at least one of the following:

the target image sample;

an image category corresponding to the target image sample; or a matching degree between the target image sample and the target region image.

17. The non-transitory computer-readable storage medium according to claim 13, wherein, when the computer-readable instructions are configured to cause the processor to perform locating the target region image in the endoscopic image, the computer-readable instructions are configured to cause the processor to perform:

inputting the endoscopic image into a target region locating network to obtain region coordinates, the target region locating network being a machine learning network obtained through training with second training images, and each of the second training images marked with a target region; and acquiring an image corresponding to the region coordinates in the endoscopic image as the target region image.

* * * * *